United States Patent
Dakka et al.

(10) Patent No.: US 8,829,093 B2
(45) Date of Patent: Sep. 9, 2014

(54) ALKYL AROMATIC HYDROALKYLATION FOR THE PRODUCTION OF PLASTISIZERS

(71) Applicants: Jihad Dakka, Whitehouse Station, NJ (US); Lorenzo C. DeCaul, Langhorne, PA (US); Christine A. Costello, Easton, PA (US); Edmund J. Mozeleski, Califon, NJ (US); Pierre J. Osterrieth, Brussels (BE); Diana S. Smirnova, High Bridge, NJ (US); Stephen Zushma, Clinton, NJ (US); Allen D. Godwin, Seabrook, TX (US)

(72) Inventors: Jihad Dakka, Whitehouse Station, NJ (US); Lorenzo C. DeCaul, Langhorne, PA (US); Christine A. Costello, Easton, PA (US); Edmund J. Mozeleski, Califon, NJ (US); Pierre J. Osterrieth, Brussels (BE); Diana S. Smirnova, High Bridge, NJ (US); Stephen Zushma, Clinton, NJ (US); Allen D. Godwin, Seabrook, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 5 days.

(21) Appl. No.: 13/751,835

(22) Filed: Jan. 28, 2013

(65) Prior Publication Data
US 2014/0213709 A1    Jul. 31, 2014

(51) Int. Cl.
*C08K 5/00*    (2006.01)
*C08K 5/101*   (2006.01)
*C08K 5/12*    (2006.01)

(52) U.S. Cl.
CPC .. *C08K 5/12* (2013.01); *C08K 5/101* (2013.01)
USPC ......................................... 524/287; 524/284

(58) Field of Classification Search
USPC ....................................................... 524/287
See application file for complete search history.

(56) References Cited

U.S. PATENT DOCUMENTS

| | | | |
|---|---|---|---|
| 2,520,084 A * | 8/1950 | Dazzi ............................. | 524/290 |
| 3,296,065 A * | 1/1967 | O'Brien et al. ................ | 162/158 |
| 4,294,976 A | 10/1981 | Itatani et al. | |
| 5,138,022 A | 8/1992 | Mang et al. | |
| 6,274,756 B1 | 8/2001 | Caers et al. | |
| 6,482,972 B1 | 11/2002 | Bahrmann et al. | |
| 6,740,254 B2 | 5/2004 | Zhou et al. | |
| 6,777,514 B2 | 8/2004 | Patil et al. | |
| 7,297,738 B2 | 11/2007 | Gosse et al. | |
| 8,115,034 B2 | 2/2012 | Godwin et al. | |
| 2006/0247461 A1 | 11/2006 | Schlosberg et al. | |
| 2008/0242895 A1 | 10/2008 | Godwin et al. | |
| 2010/0159177 A1 | 6/2010 | Dakka et al. | |
| 2011/0151162 A1 | 6/2011 | Dakka et al. | |
| 2012/0108726 A1 | 5/2012 | Godwin et al. | |
| 2012/0108874 A1 | 5/2012 | Gralla et al. | |

FOREIGN PATENT DOCUMENTS

| | | |
|---|---|---|
| SU | 412182 A | 8/1974 |
| WO | 9932427 A1 | 1/1999 |
| WO | 03029339 A1 | 4/2003 |
| WO | 2004046078 A1 | 6/2004 |

OTHER PUBLICATIONS

Zhang et al., J. Comb. Chem., 8, 890-896, 2006.*
"Synthesis of dialkyl diphenates and their properties", Shioda et al., Yuki Gosei Kagaku Kyokaishi (1959), 17; ISSN: 0037-9980 (English Abstract Only).
"Esters of diphenic acid and their plasticizing properties", Kulev et al., Izvestiya Tomskogo Politekhnicheskogo Instituta (1961) 111; ISSN: 0368-0487 (English Abstract Only).
Ukhopadhyay, Sudip; Rothenberg, Gadi; Gitis, Diana; Sasson, Yoel. Casali Institute of Applied Chemistry, Hebrew University of Jerusalem, Israel. Journal of Organic Chemistry (2000), 65(10), 3107-3110. Publisher: American Chemical Society.
"Plasticizers," A. D. Godwin, in Applied Polymer Science 21st Century, edited by C. D. Craver and C. E. Carraher, Elsevier (2000); pp. 157-175.
U.S. Appl. No. 61/203,626, Dec. 24, 2008, Dakka et al.
U.S. Appl. No. 61/040,480, Mar. 28, 2008, Godwin et al.
U.S. Appl. No. 61/781,116, Mar. 14, 2013, Bai et al.
Clary, International Journal of Organic Chemistry, 2013, 3, 143-147.
Cheng, J.C. et al., "*Direct Alkylation of Aromatic Hydrocarbons with n-Paraffin*", Mobil Technology Company, SRC Progress Memo 97-310-006, Dec. 1, 1997, pp. 1-43.
Stevenson, S.A. et al., "*Conversion of Benzene to Phenylcyclohexane over a Tungsten/Zirconia Catalyst*", Mobil Technology Company, SRC Progress Memo 97M-0392, May 7, 1997, pp. 1-25.
Zhang, W. et al. "*Automation of Fluorous Solid-Phase Extraction for Parallel Synthesis*", J. Comb. Chem. (2006) pp. 890-896.

* cited by examiner

*Primary Examiner* — Hui Chin

(57) ABSTRACT

Provided are compounds of the following:

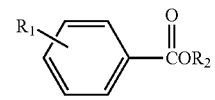

wherein $R_1$ is a saturated or unsaturated cyclic hydrocarbon optionally substituted with an alkyl and/or an OXO-ester, and $R_2$ is the residue of a $C_4$ to $C_{14}$ OXO-alcohol. Also provided are processes for making the compounds and plasticized polymer compositions containing said compounds.

40 Claims, No Drawings

ALKYL AROMATIC HYDROALKYLATION FOR THE PRODUCTION OF PLASTISIZERS

FIELD

This disclosure relates to a route to aromatic OXO multi-ester plasticizers.

BACKGROUND

Plasticizers are incorporated into a resin (usually a plastic or elastomer) to increase the flexibility, workability, or distensibility of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

Plasticizers can be characterized on the basis of their chemical structure. The most important chemical class of plasticizers is phthalic acid esters, which accounted for 85% worldwide of PVC plasticizer usage in 2002.

Others are esters based on cyclohexanoic acid. In the late 1990's and early 2000's, various compositions based on cyclohexanoate, cyclohexanedioates, and cyclohexanepolyoate esters were said to be useful for a range of goods from semi-rigid to highly flexible materials. See, for instance, WO 99/32427, WO 2004/046078, WO 2003/029339, WO 2004/046078, U.S. Application No. 2006-0247461, and U.S. Pat. No. 7,297,738.

Other include esters based on benzoic acid (see, for instance, U.S. Pat. No. 6,740,254, and also co-pending, commonly-assigned, U.S. Provisional Patent Application No. 61/040,480, filed Mar. 28, 2008 and polyketones, such as described in U.S. Pat. No. 6,777,514; and also co-pending, commonly-assigned, U.S. Patent Publication No. 2008/0242895, filed Mar. 28, 2008. Epoxidized soybean oil, which has much longer alkyl groups ($C_{16}$ to $C_{18}$) has been tried as a plasticizer, but is generally used as a PVC stabilizer. Stabilizers are used in much lower concentrations than plasticizers. Copending and commonly assigned U.S. Provisional Patent Application No. 61/203,626, filed Dec. 24, 2008, discloses triglycerides with a total carbon number of the triester groups between 20 and 25, produced by esterification of glycerol with a combination of acids derived from the hydroformylation and subsequent oxidation of $C_3$ to $C_9$ olefins, having excellent compatibility with a wide variety of resins U.S. Pat. No. 2,520,084 to Dazzi discloses plasticized vinyl chloride polymers using esters of phenyl benzoic acids and aliphatic hydrocarbon alcohols as plasticizers. Suitable esters are 2-ethylhexyl m-phenylbenzoate, the corresponding para- and ortho-phenylbenzoates, or mixtures thereof, and the various phenylbenzoates of n-hexyl, 2-methyheptyl, dodecyl, dimethylheptyl, 2-butoxyethyl, and isooctyl alcohols, and other homologous straight and branched alcohols having 8 to 14 atoms. The butoxyethyl and 2-ethythexyl esters of phenylbenzoic acid are exemplified.

"Esters of diphenic acid and their plasticizing properties", Kulev et al., *Izvestiya Tomskogo Politekhnicheskogo Instituta* (1961) 111, discloses diisoamyl diphenate, bis(2-ethylhexyl diphenate and mixed heptyl, octyl and nonyl diphenates, prepared by esterification of diphenic acid, useful as plasticizers for vinyl chloride.

"Synthesis of dialkyl diphenates and their properties", Shioda et al., *Yuki Gosei Kagaku Kyokaishi* (1959), 17, discloses dialkyl diphenates of $C_1$ to $C_8$ alcohols, useful as plasticizers for poly(vinyl chloride) formed by converting diphenic acid to diphenic anhydride and esterifying the diphenic anhydride, necessarily resulting in 2,2'-substituted diesters of diphenic anhydride.

Thus what is needed is a method of making a general purpose plasticizer having suitable melting or chemical and thermal stability, pour point, glass transition, increased compatibility, good performance and low temperature properties.

SUMMARY

In one aspect, the present application provides compounds of the formula

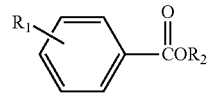

wherein $R_1$ is a saturated or unsaturated cyclic hydrocarbon optionally substituted with an alkyl and/or an OXO-ester, and $R_2$ is a hydrocarbon residue of a $C_4$ to $C_{14}$ OXO-alcohol.

In another aspect, the present application provides a process for making compounds of the formula:

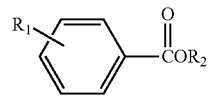

wherein $R_1$ is a cyclic hydrocarbon optionally substituted with an alkyl and/or an OXO-ester, and $R_2$ is a hydrocarbon residue of a $C_4$ to $C_{14}$ OXO-alcohol, comprising the steps of: reacting benzene or alkylated benzene under conditions appropriate to form alkylated biphenyl; optionally alkylating biphenyl to form said alkylated biphenyl; oxidizing the alkyl group(s) on said alkylated biphenyl to form at least one acid group; and reacting said acid group(s) with an OXO-alcohol under esterification conditions to form said compounds.

In another aspect, the present application provides a polymer composition comprising a thermoplastic polymer and at least one plasticizer of the formula:

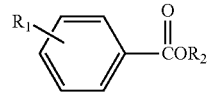

wherein $R_1$ is a saturated and unsaturated cyclic hydrocarbon optionally substituted with an alkyl and/or an OXO-ester, and $R_2$ is a hydrocarbon residue of a $C_4$ to $C_{14}$ OXO-alcohol.

DETAILED DESCRIPTION

All numerical values within the detailed description and the claims herein are modified by "about" or "approximately" the indicated value, and take into account experimental error and variations that would be expected by a person having ordinary skill in the art.

There is an increased interest in developing new plasticizers which possess good plasticizer performance characteristics but are still competitive economically. The present disclosure is directed towards mono- or diester plasticizers, particularly OXO-ester plasticizers, that can be made from low cost feeds and employ fewer manufacturing steps in order to meet economic targets.

It has been determined that compounds of the general formula

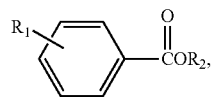

wherein $R_1$ is a saturated or unsaturated cyclic hydrocarbon, optionally substituted with an alkyl and/or an OXO-ester, and $R_2$ is the residue of a $C_4$ to $C_{14}$ OXO-alcohol, are particularly useful as plasticizers for conventional polymer plastics.

One route to plasticizers of the present disclosure is by combination of two benzene molecules, by controlled hydrogenation, as follows:

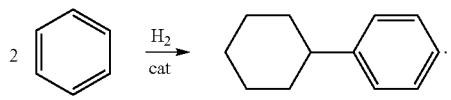

According to this method, the cyclohexyl benzene so formed can be optionally dehydrogenated to form biphenyl as follows:

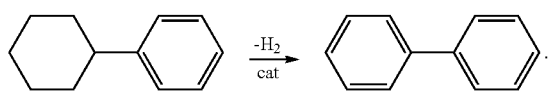

In either case, the aromatic ring(s) are subsequently alkylated with an alcohol, such as methanol, which acts to add one or more methyl groups to the ring(s), followed by oxygenation of the pendant methyl group(s) to form carboxylic acid group(s), and subsequently esterified with an alcohol, ROH, to form the mono- or diesters of the present disclosure and subsequently hydrogenated with an hydrogen over hydrogenation catalyst, to form one or more saturated ring:

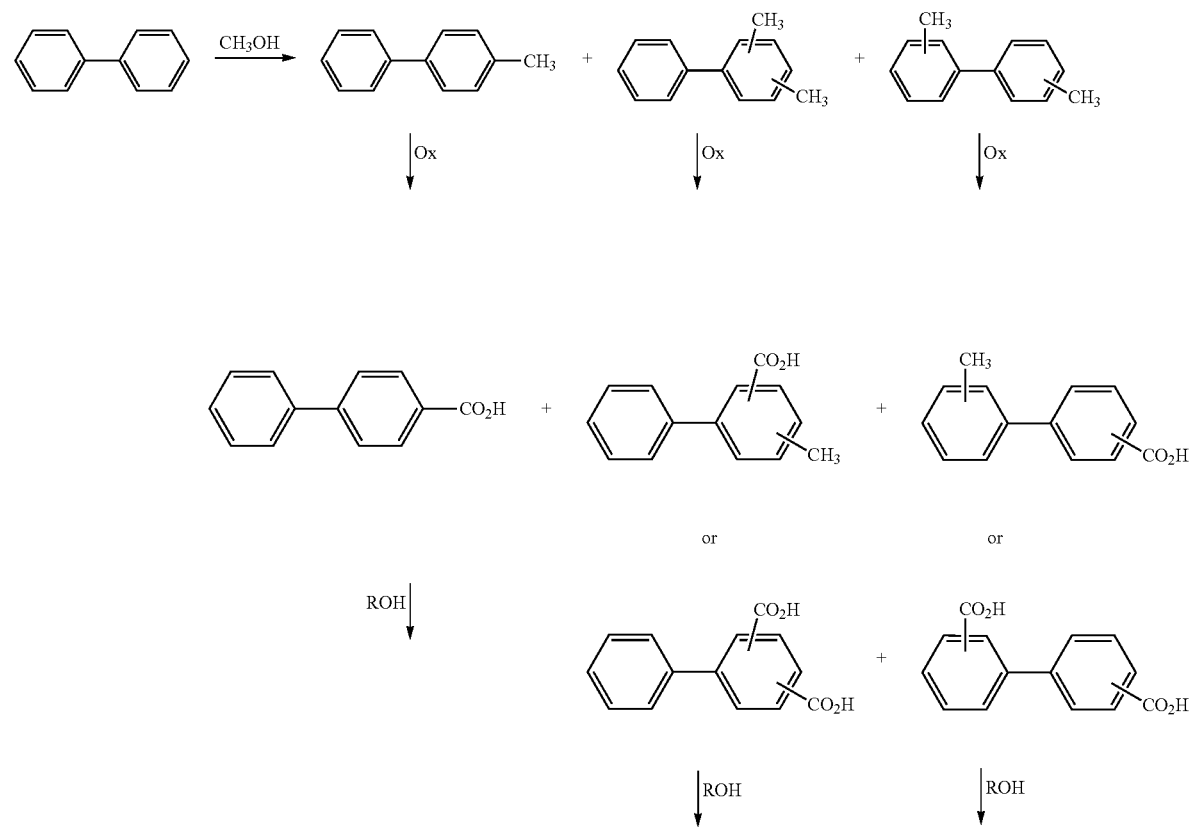

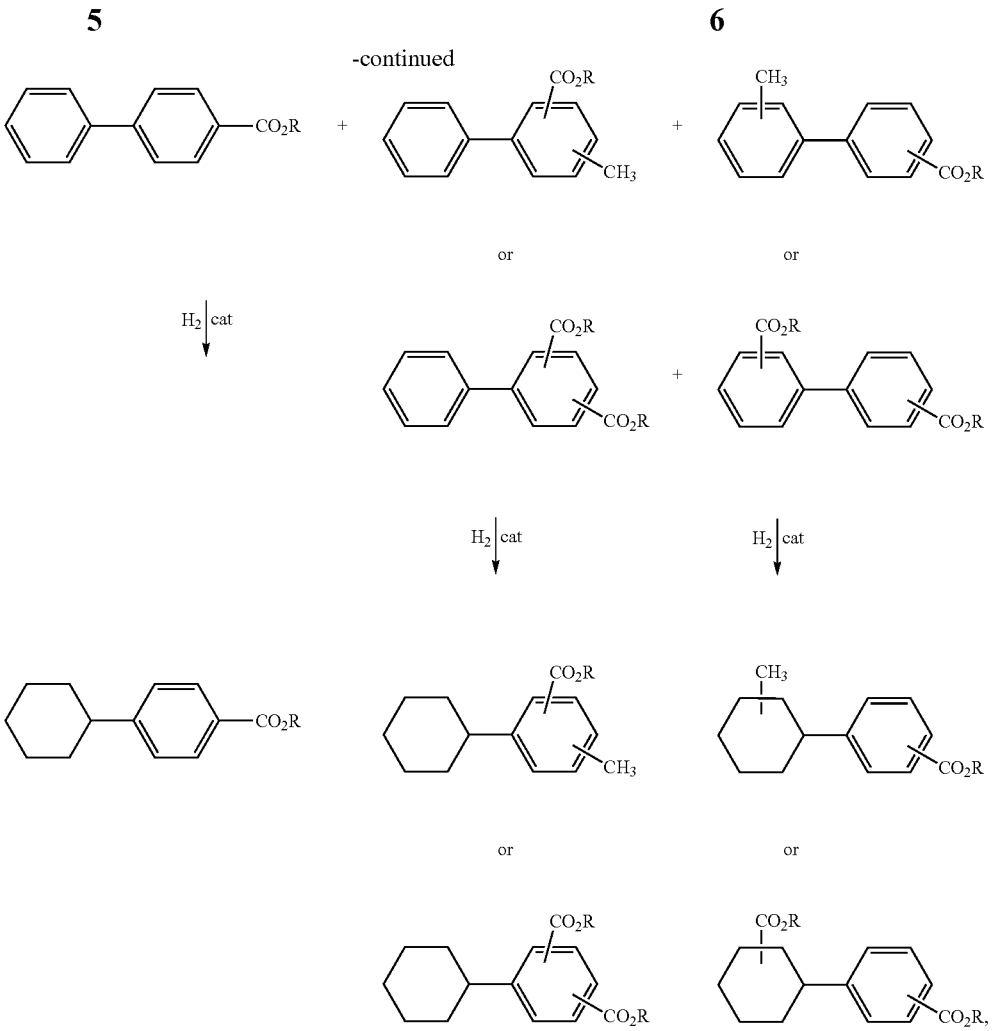

wherein ROH is a branched alcohol, preferably an OXO-alcohol, even more preferably a $C_4$ to $C_{14}$ OXO-alcohol.

Another route to plasticizers of the present disclosure is by oxidative coupling of two benzene molecules to form biphenyl, as follows:. For benzene coupling: Ukhopadhyay, Sudip; Rothenberg, Gadi; Gitis, Diana; Sasson, Yoel. Casali Institute of Applied Chemistry, Hebrew University of Jerusalem, Israel. Journal of Organic Chemistry (2000), 65(10), 3107-3110. Publisher: American Chemical Society, incorporated herein by reference Similarly to the first process, the biphenyl molecule is then alkylated, for example, with an alcohol, such as methanol, to add one or more methyl groups to the ring(s), followed by oxygenation of the pendant methyl group(s) to form carboxylic acid group(s), and subsequently esterified with an alcohol, ROH, to form the mono- or diesters of the present disclosure and subsequently hydrogenated with an hydrogen over hydrogenation catalyst, to form one or more saturated rings.

Of course, a similar process can be followed utilizing an alkyl aromatic, such as toluene as the starting material in place of benzene:

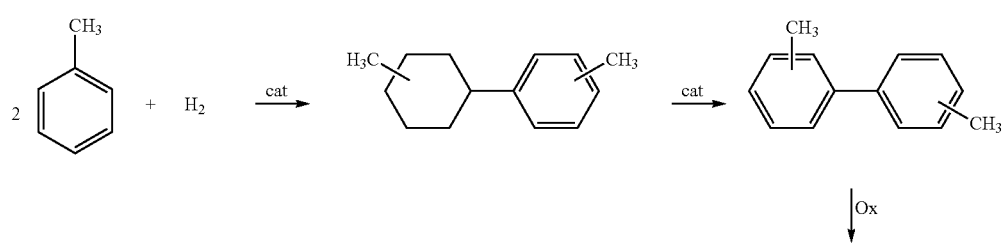

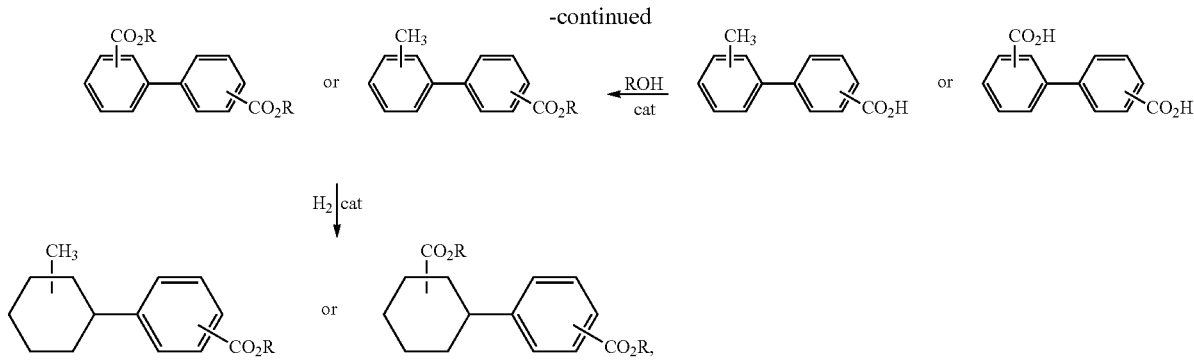

wherein ROH is a branched alcohol, preferably an OXO-alcohol, even more preferably a $C_4$ to $C_{14}$ OXO-alcohol. Either monoesters or diesters can be formed. Likewise, by appropriate control of the oxidation step so as to oxidize only one of the pendant methyl groups, monoester compounds of the following general formula can be formed:

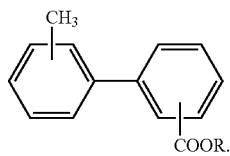

Alternatively, one mole of toluene can be hydrogenated to form methyl cyclohexene, and then the methyl cyclohexene used to alkylate another mole of toluene, followed by dehydrogenation to form dimethyl biphenyl.

In a more preferred embodiment, the resulting alkylated aromatic compound is oxidized to acid/diacid then esterified with OXO-alcohols, which are mixed linear and branched alcohol isomers, the formation of which is described in more detail below.

"OXO-alcohols" are isomeric mixtures of branched, organic alcohols. "OXO-esters" are compounds having at least one functional ester moiety within its structure derived from esterification of a carboxylic acid portion or moiety of a compound with an OXO-alcohol.

OXO-alcohols can be prepared by hydroformylating olefins, followed by hydrogenation to form the alcohols. "Hydroformylating" or "hydroformylation" is the process of reacting a compound having at least one carbon-carbon double bond (an olefin) in an atmosphere of carbon monoxide and hydrogen over a cobalt or rhodium catalyst, which results in addition of at least one aldehyde moiety to the underlying compound. U.S. Pat. No. 6,482,972, which is incorporated herein by reference in its entirety, describes the hydroformylation (OXO) process. The resulting OXO-alcohols consist of multiple isomers of a given chain length due to the various isomeric olefins obtained in the oligomerization process, described below, in tandem with the multiple isomeric possibilities of the hydroformylation step.

Typically, the isomeric olefins are formed by light olefin oligomerization over heterogenous acid catalysts, such as by propylene and/or butene oligomerization over solid phosphoric acid or zeolite catalysts. The light olefins are readily available from refinery processing operations. The reaction results in mixtures of longer-chain, branched olefins, which are subsequently formed into longer chain, branched alcohols, as described below and in U.S. Pat. No. 6,274,756, incorporated herein by reference in its entirety. Olefins for hydroformulation can also be prepared by dimerization of propylene or butenes through commercial processes such as the IFP Dimersol™ process or the Huls (Evonik) Octol™ process.

Branched aldehydes are then produced by hydroformylation of the isomeric olefins. The resulting branched aldehydes can then be recovered from the crude hydroformylation product stream by fractionation to remove unreacted olefins. These branched aldehydes can then be hydrogenated to form alcohols (OXO-alcohols). Single carbon number alcohols can be used in the esterification of the acids described above, or differing carbon numbers can be used to optimize product cost and performance requirements. The "OXO" technology provides cost advantaged alcohols. Other options are considered, such as hydroformylation of $C_4$-olefins to $C_5$-aldehydes, followed by hydrogenation to $C_5$-alcohols, or aldehyde dimerization followed by hydrogenation to $C_{10}$ alcohols.

"Hydrogenating" or "hydrogenation" is addition of hydrogen ($H_2$) to a double-bonded functional site of a molecule, such as in the present case the addition of hydrogen to the aldehyde moieties of a di-aldehyde, to form the corresponding di-alcohol, and saturation of the double bonds in an aromatic ring. Conditions for hydrogenation of an aldehyde are well-known in the art and include, but are not limited to temperatures of 0-300° C., pressures of 1-500 atmospheres, and the presence of homogeneous or heterogeneous hydrogenation catalysts such as, but not limited to Pt/C, Pt/$Al_2O_3$ or Pd/$Al_2O_3$ and Ni.

Alternatively, the OXO-alcohols can be prepared by aldol condensation of shorter-chain aldehydes to form longer chain aldehydes, as described in U.S. Pat. No. 6,274,756, followed by hydrogenation to form the OXO-alcohols.

"Esterifying" or "esterification" is reaction of a carboxylic acid moiety, such as an anhydride, with an organic alcohol moiety to form an ester linkage. Esterification conditions are well-known in the art and include, but are not limited to, temperatures of 0-300° C., and the presence or absence of homogeneous or heterogeneous esterification catalysts such as Lewis or Brønsted acid catalysts.

As discussed above, the resulting OXO-alcohols can be used individually or together in alcohol mixtures having different chain lengths, or in isomeric mixtures of the same carbon chain length to make mixed esters for use as plasticizers. This mixing of carbon numbers and/or levels of branching can be advantageous to achieve the desired compatibility with PVC for the respective core alcohol or acid used for the polar moiety end of the plasticizer, and to meet other plasticizer performance properties. The preferred OXO-alcohols are those having from 5 to 10 carbons, more preferably $C_5$ to $C_{10}$ alcohols, and even more preferably $C_6$ to $C_{10}$ alcohols.

In one embodiment the preferred OXO-alcohols are those which have an average branching of from 0.2 to 5.0 branches per molecule, and from 0.35 to 5.0 methyl branches per molecule, or even from 1.3 to 5.0 methyl branches per molecule. In a more preferred embodiment, the alcohols have from 0.05 to 0.4 branches per residue at the alcoholic beta carbon.

Typical branching characteristics of OXO-alcohols are provided in Table 1, below.

TABLE 1

$^{13}$C NMR Branching Characteristics of Typical OXO-Alcohols.

| OXO-Alcohol | Avg. Carbon No. | % of α-Carbons w/ Branches[a] | β-Branches per Molecule[b] | Total Methyls per Molecule[c] | Pendant Methyls per Molecule[d] | Pendant Ethyls per Molecule |
|---|---|---|---|---|---|---|
| $C_4$[e] | 4.0 | 0 | 0.35 | 1.35 | 0.35 | 0 |
| $C_5$[f] | 5.0 | 0 | 0.30 | 1.35 | 0.35 | 0 |
| $C_6$ | — | — | — | — | — | — |
| $C_7$ | 7.2 | 0 | 0.13 | 2.2 | — | 0.04 |
| $C_8$ | 8.0 | 0 | 0.08 | 2.6 | — | — |
| $C_9$ | 9.3 | 0 | 0.09 | 3.1 | — | — |
| $C_{10}$ | 10.1 | 0 | 0.08 | 3.1 | — | — |
| $C_{12}$ | 11.8 | 0 | 0.09 | 3.9 | — | — |
| $C_{13}$ | 12.7 | 0 | 0.09 | 3.9 | — | — |

— Data not available.
[a] —COH carbon.
[b] Branches at the —CH$_2$OH carbon.
[c] This value counts all methyl groups, including C$_1$ branches, chain end methyls, and methyl endgroups on C$_2$+ branches.
[d] C$_1$ branches only.
[e] Calculated values based on an assumed molar isomeric distribution of 65% n-butanol and 35% isobutanol (2-methylpentanol).
[f] Calculated values based on an assumed molar isomeric distribution of 65% n-pentanol, 30% 2-methylbutanol, and 5% 3-methylbutanol.

In general, for every polymer to be plasticized, a plasticizer is required with the correct balance of solubility, volatility and viscosity to have acceptable plasticizer compatibility with the resin. In particular, if the 20° C. kinematic viscosity is higher than 250 mm$^2$/sec as measured by the appropriate ASTM test, or alternately if the 20° C. cone-and-plate viscosity is higher than 250 cP, this will affect the plasticizer processability during formulation, and can require heating the plasticizer to ensure good transfer during storage and mixing of the polymer and the plasticizer. Volatility is also a very critical factor which affects the long-term plasticizer formulation stability. Highly volatile plasticizers can migrate from the plastic resin matrix, thus losing effectiveness in applications requiring long term stability/flexibility. Relative plasticizer volatility in a resin matrix can be roughly predicted by neat plasticizer weight loss at 220° C. using Thermogravimetric Analysis.

We have found that when C4 to $C_{13}$ OXO-alcohols are used as reactants for the esterification reactions described above, the resulting OXO-esters are in the form of relatively high-boiling liquids (having low volatility), which are readily incorporated into polymer formulations as plasticizers.

Any of the esters can have $R_1$ and $R_2$ which contain mixed alkyl isomer residues of $C_4$ to $C_{13}$ OXO-alcohols, and can be used as plasticizers for polymers, such as vinyl chloride resins, polyesters, polyurethanes, ethylene-vinyl acetate copolymer, rubbers, poly(meth)acrylics and combinations thereof, preferably polyvinylchloride.

The following examples are meant to illustrate the present disclosure and inventive processes, and provide where appropriate, a comparison with other methods, including the products produced thereby. Numerous modifications and variations are possible and it is to be understood that within the scope of the appended claims, the disclosure can be practiced otherwise than as specifically described herein.

EXAMPLES

General Procedure For Esterification

Into a four necked 1000 ml round bottom flask equipped with an air stirrer, nitrogen inductor, thermometer, Dean-Stark trap and chilled water cooled condenser were added an aromatic mono or (di)acid, and the OXO-alcohol(s). The Dean-Stark trap was filled with the OXO-alcohol(s). The reaction mixture was heated to 220° C. with air stirring under a nitrogen sweep. The water that was produced was collected in the Dean-Stark trap was drained frequently. The theoretical weight of water was obtained in 3 hours at 220° C. indicating 96% conversion. The reaction mixture was heated longer to achieve complete conversion to the diester. Excess alcohols plus some monoesters (in the case of diester synthesis) were removed by distillation. The crude residual product was optionally treated with decolorizing charcoal with stirring at room temperature overnight. The mixture was then filtered twice to remove the charcoal.

Example 1

Esterification of 4-phenyl-benzoic acid with Oxo-$C_{10}$ alcohols

Into a 4-necked 500 ml round bottom flask equipped with an air stirrer, thermometer, $N_2$ inductor, Dean-Stark trap and chilled water cooled condenser were added 4-phenyl-benzoic acid (101.8 g, 0.514 mole), OXO-$C_{10}$ alcohols (163 g, 1.027 mole), and OXO-$C_{10}$ alcohols (15.5 g, 0.098 moles) was added to the Dean-Stark trap. The reaction mixture was heated at total of 13 hours at 208-220° C. with gas chromatographic (GC) sampling. The product was then concentrated using a Claisen adapter, chilled water cooled condenser and receiving flask. The crude product was a clear light yellow liquid, 99.5% purity by GC.

Example 2

Esterification of 4-phenylbenzoic acid with OXO-$C_9$ alcohols

Into a 4-necked 500 ml round bottom flask equipped with an air stirrer, thermometer, N2 inductor, Dean-Stark trap and chilled water cooled condenser were added 4-phenylbenzoic acid (138 g, 0.6962 mole), OXO-$C_9$ alcohols (201.1 g, 1.3924 mole) and xylenes (21.5 g, 0.202 mole). The reaction mixture was heated at total of 7 hours at 185-220° C. with GC sampling. The product was concentrated using a Claisen adapter, chilled water cooled condenser and receiving flask. The concentrated product was dissolved in an equal weight of toluene (180 g) and was washed twice with 100 g of a 3 wt % sodium hydroxide solution followed by distilled water (100 g). The upper toluene phase was then dried over magnesium sulfate, filtered and the toluene removed on a rotary evaporator. The concentrated product was a clear and colorless liquid with a purity of 99.5% monoesters by GC.

Example 3

Esterification of 3-phenyl-benzoic acid with Oxo-$C_{10}$ alcohols NGP 77

Into a 4-necked 500 ml round bottom flask equipped with an air stirrer, thermometer, $N_2$ inductor, Dean-Stark trap and chilled water cooled condenser were added biphenyl-3-carboxylic acid (50.0 g, 0.2522 mole), OXO-$C_{10}$ alcohols (79.7 g, 0.5044 mole), and xylenes (75 g, 0.706 moles) were added to the Dean-Stark trap. The reaction mixture was heated a total of 19 hours at 156-192° C. The product was concentrated using a Claisen adapter, chilled water cooled condenser and receiving flask. The concentrated product was dissolved in an equal weight of toluene (77 g) and was washed three times with 25 g of a 3 wt % sodium hydroxide solution followed by distilled water (25 g) twice. The upper toluene phase was then dried over magnesium sulfate, filtered and distilled overhead. The boiling point of the pure product was 175-183° C./0.27-0.28 mm vacuum. The purity of the distilled product was 99.2% by GC.

Example 4

Esterification of 2-phenyl-benzoic acid with OXO-$C_9$ alcohols NGP 52

Into a 4-necked 500 ml round bottom flask equipped with an air stirrer, thermometer, $N_2$ inductor, Dean-Stark trap and chilled water cooled condenser were added biphenyl-2-carboxylic acid (99.4 g, 0.502 mole), OXO-$C_9$ alcohols (144.4 g, 1.003 mole), and OXO-$C_9$ alcohols (20 g, 0.14 moles) were added to the Dean-Stark trap. The reaction mixture was heated at total of 7 hours at 205-208° C. with GC sampling. The product was distilled using a Claisen adapter, chilled water cooled condenser and receiving flask. Two of the heart cuts were combined and dissolved in an equal weight of toluene (121.7 g) and was washed twice with 50 g of a 3 wt % sodium hydroxide solution followed by distilled water (50 g). The upper toluene phase was then dried over magnesium sulfate, filtered then treated with decolorizing charcoal with stirring at room temperature for 2 hours. The product was filtered twice to remove all the charcoal. The toluene was then removed on the rotary evaporator. The clear and coloress product was isolated with a, purity of 99.5% (by GC) monoesters.

Example 5

Blend of Example 1, 3 and 4

The following blend of pure monoesters was prepared: the ortho ester or biphenyl-2-carboxylic acid plus OXO-$C_9$ alcohols (7.5 grams or 25 wt %), the meta ester biphenyl-3-carboxylic acid plus OXO-$C_{10}$ alcohols (15.0 grams or 50 wt %) and the para monoester or biphenyl-4-carboxylic acid plus OXO-$C_{10}$ alcohols (7.5% or 25%).

Example 6

Esterification of 4-cyclohexyl benzoic acid with Oxo-$C_{10}$ alcohols

Into a 4-necked 500 ml round bottom flask equipped with an air stirrer, thermometer, $N_2$ inductor, Dean-Stark trap and chilled water cooled condenser were added 4-cyclohexyl benzoic acid (100.64 g, 0.493 mole), OXO-$C_{10}$ alcohols (156.5 g, 0.986 mole), and OXO-$C_{10}$ alcohols (15.5 g, 0.098 moles) were added to the Dean-Stark trap. The reaction mixture was heated at total of 10 hours at 217-220° C. with GC sampling. The product was then concentrated using a Claisen adapter, chilled water cooled condenser and receiving flask. The crude product was a clear & colorless liquid, 99.2% purity (by GC).

Example 7

Blend of Example 1 and 6 NGP 75, 90, 91, 92

The following four blends (by weight) were prepared containing the monoester of 4-phenylbenzoic acid plus OXO-$C_{10}$ alcohols (example 1) and the monoester of 4-cyclohexylbenzoic acid plus OXO-$C_{10}$ alcohols (example 6):

7a: NGP-75: blend of example 1 (70%) plus example 6 (30%),
7b: NGP-90: blend of example 1 (70%) plus example 6 (30%),
7c: NGP-91: blend of example 1 (50%) plus example 6 (50%),
7d: NGP-92: blend of example 1 (30%) plus example 6 (70%).

Example 8

Esterification of 4'-methylbiphenyl-4-carboxylic acid with Oxo-$C_9$ alcohols

Into a 4-necked 500 ml round bottom flask equipped with an air stirrer, thermometer, $N_2$ inductor, Dean-Stark trap and chilled water cooled condenser were added 4-methylbiphenyl-4-carboxylic acid (100 g, 0.47114 mole), OXO-$C_9$ alcohols (136.1 g, 0.9423 mole) and toluene (50 g, 0.54 mole). The reaction mixture was heated at total of 6 hours at 187-221° C. with GC sampling. The product was then distilled using a Claisen adapter, chilled water cooled condenser and receiving flask. The product distilled at 184-185° C./0.10 mm and was a clear, essentially colorless liquid with 99.6% purity (by GC).

Example 9

Esterification of 4'-methylbiphenyl-2-carboxylic acid with Oxo-C9 alcohols

Into a 4-necked 1000 ml round bottom flask equipped with an air stirrer, thermometer, $N_2$ inductor, Dean-Stark trap and chilled water cooled condenser were added 2-(p-tolyl)benzoic acid (191.9 g, 0.9042 mole), OXO-$C_9$ alcohols (261.12 g, 1.8087 mole) and xylenes (19.4 g, 0.18 mole). The reaction mixture was heated a total of 22 hours at 207-214° C. with GC sampling. The product was then distilled using a Claisen adapter, chilled water cooled condenser and receiving flask. The product distilled at 145-162° C./0.10 mm and was a clear, essentially colorless liquid of 99.86% purity (by GC).

Example 10

Esterification of 2'-methyl-3-biphenylcarboxylic acid with OXO-$C_{10}$ alcohols Into a 4-necked 500 ml round bottom flask equipped with an air stirrer, thermometer, $N_2$ inductor, Dean-Stark trap and chilled water cooled condenser were added 2'-methyl-3-biphenylcarboxylic acid (51 g, 0.24 mole), OXO-$C_{10}$ alcohols (76 g, 0.481 mole) and xylenes (34.3 g, 0.323 mole). The reaction mixture was heated at total of 15 hours at 145-182° C. with GC sampling. The product was concentrated using a Claisen adapter, chilled water cooled condenser and receiving flask. The concentrated product was dissolved in an equal weight of toluene (63.1 g) and was washed twice with 30 g of a 3 wt % sodium hydroxide solution followed by distilled water (30 g). The upper toluene phase was then dried over magnesium sulfate, filtered and distilled. The monoester distilled at Bp=175-182° C./0.10 mm. A clear off white liquid was obtained with a purity of 99.42% (by GC).

Example 11

Preparation of 4'-methyl-3-biphenylcarboxylic acid with OXO-$C_{10}$ alcohols (NGP-85): Decyl 3-bromobenzoate was Prepared from the Condensation of 3-bromobenzoic acid and OXO-$C_{10}$ alcohols by Refluxing in Benzene with Water Removal via a Dean-Stark Trap. The Ester was Purified by Distillation $^1$H NMR (400 MHz, CDCl$_3$) δ 0.87-1.77 (m, 21 H), 4.32 (m, 2 H), 7.32 (m, 1 H), 7.67 (m, 1 H), 7.98 (m, 1 H), 8.18 (s, 1 H). In a 3-neck flask, Decyl 3-bromobenzoate (1 equiv) and p-tolylboronic acid (1.2 equiv) were dissolved in toluene to make a 0.2 M solution with respect to the bromobenzoic ester and the mixture degassed with N$_2$. A 2 M, degassed solution of sodium carbonate (2.5 equiv) in H$_2$O:MeOH (4:1) was added. Palladium tetrakistriphenylphosphine (0.01 equiv) was added and the mixture refluxed until completion. The reaction was cooled and the layers separated. The aqueous layer was extracted with ethyl acetate and combined organic layers were washed with brine, dried over MgSO$_4$, filtered and concentrated under reduced pressure. Purification of the resulting crude oil was achieved by vacuum distillation $^1$H NMR (400 MHz, CDCl$_3$) δ 0.80-1.87 (m, 20 H), 2.45 (s, 3 H), 4.39 (m, 2 H), 7.31 (d, J=8.0 Hz, 2 H), 7.56 (m, 3 H), 7.80 (m, 1 H), 8.05 (m, 1 H), 8.32 (s, 1 H).

Example 12

Preparation of 2'-methyl-4-biphenylcarboxylic acid with OXO-C10 alcohols (NGP-86)

Decyl 4-bromobenzoate was prepared from the condensation of 4-bromobenzoic acid and OXO-C10 alcohols by refluxing in benzene with water removal via a Dean-Stark trap, then purified by distillation. Decyl 2-bromobenzoate was coupled with o-tolylbronic acid as described in Example 11. Spectral data is as follows: decyl 2'-methylbiphenyl-4-carboxylate: 1H NMR (400 MHz, CDCl3) 0.85-1.91 (m, 19 H), 2.33 (s, 3 H), 4.43 (m, 2H), 7.30 (m, 4 H), 7.44 (d, J=8.0 Hz, 2 H), 8.15 (m, 2 H).

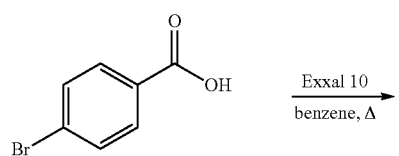

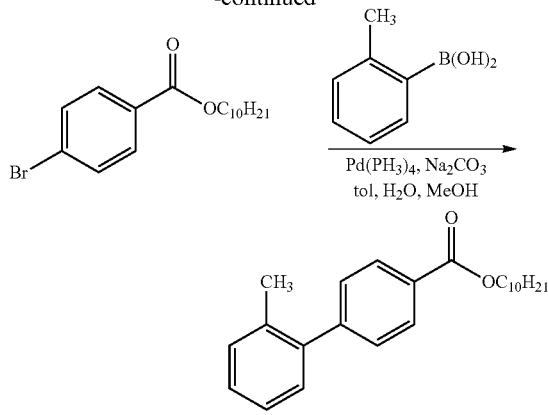

Example 13

Preparation of 3'-methyl-4-biphenylcarboxylic acid with OXO-$C_{10}$ alcohols (NGP-87): Decyl 4-bromobenzoate was Prepared from the Condensation of 4-bromobenzoic acid and OXO-$C_{10}$ alcohols by Refluxing in Benzene with Water Removal via a Dean-Stark Trap $^1$H NMR (400 MHz, CDCl$_3$) δ 0.86-1.76 (m, 20 H), 4.30 (m, 2 H), 7.57 (d, J=8.0 Hz, 2 H), 7.90 (dd, J=2.2, 8.6 Hz, 2H). Decyl 4-bromobenzoate was coupled with m-tolylboronic acid as described in Example 11: $^1$H NMR (400 MHz, CDCl$_3$) δ 0.88-1.80 (m, 19 H), 2.44 (s, 3 H), 4.33 (m, 2 H), 7.22 (d, J=8.0 Hz, 1 H), 7.36 (m, 1 H), 7.45 (m, 1 H), 7.66 (d, J=8.0 Hz, 2 H), 8.11 (m, 2 H); $^{13}$C NMR (100 MHz, CDCl$_3$) 10.9-39.4 (9 C), 21.7, 65.3, 124.5-130.2 (8 C), 138.7 (2 C), 140.2, 145.8, 166.8.

Example 14

Preparation of 3'-methyl-4-biphenylcarboxylic acid with OXO-$C_9$ alcohols (NGP-88): Nonyl 4-bromobenzoate was Prepared from the Condensation of 4-bromobenzoic acid and OXO-$C_9$ alcohols by Refluxing in Benzene with Water Removal via a Dean-Stark Trap $^1$H NMR (400 MHz, CDCl$_3$) δ 0.87-1.78 (m, 19 H), 4.31 (m, 2 H), 7.57 (d, J=8.4 Hz, 2 H), 7.90 (dd, J=2.9, 9.4 Hz, 2H). Nonyl 4-bromobenzoate was coupled with m-tolylboronic acid as described in Example 11: $^1$H NMR (400 MHz, CDCl$_3$) δ 0.90-1.78 (m, 19 H), 2.45 (s, 3 H), 4.38 (m, 2 H), 7.22 (d, J=8.4 Hz, 1 H), 7.36 (m, 1 H), 7.45 (m, 2 H), 7.66 (d, J=8.0 Hz, 2 H), 8.11 (m, 2 H); $^{13}$C NMR (100 MHz, CDCl$_3$) 10.9-39.4 (8 C), 21.7, 65.6, 124.5-130.2 (8 C), 138.7 (2 C), 140.2, 145.8, 166.8.

Example 15

Preparation of 3'-methyl-2-biphenylcarboxylic acid with OXO-$C_{10}$ alcohols (NGP-89): Decyl 2-bromobenzoate was Prepared from the Condensation of 2-bromobenzoic acid and OXO-$C_{10}$ alcohols by Refluxing in Benzene with Water Removal via a Dean-Stark Trap $^1$H NMR (400 MHz, CDCl$_3$) δ 0.86-1.78 (m, 23 H), 4.33 (m, 2 H), 7.35 (m, 2 H), 7.65 (m, 1 H), 7.78 (d, J=8.0 Hz, 1 H), Decyl 2-bromobenzoate was coupled with m-tolylboronic acid as described in Example 11: $^1$H NMR (400 MHz, CDCl$_3$) δ 0.72-1.39 (m, 21 H), 2.42 (s, 3 H), 4.07 (m, 2 H), 7.18 (m, 3 H), 7.30 (m, 1 H), 7.41 (m, 2 H), 7.53 (m, 1 H), 7.85 (d, J=8.0 Hz, 1 H).

Example 16

Preparation of 3'-methyl-3-biphenylcarboxylic acid with OXO-C$_{10}$ alcohols (NGP-96)

Decyl 3-bromobenzoate was coupled with m-tolylboronic acid as described in Example 11: $^1$H NMR (400 MHz, CDCl$_3$) δ 0.89-1.81 (m, 21 H), 2.45 (s, 3H), 4.37 (m, 2 H), 7.22 (d, J=8.0 Hz, 1 H), 7.37 (t, J=8.0 Hz, 1 H), 7.45 (d, J=8.0 Hz, 2 H), 7.52 (t, J=8.0 Hz, 1 H), 7.79 (d, J=8.0 Hz, 1 H), 8.03 (d, J=8.0 Hz, 1 H), 8.29 (s, 1 H); $^{13}$C NMR (100 MHz, CDCl$_3$) 11.6-3.4 (20 C), 21.7, 65.4, 124.4 (2 C), 128.1, 128.4 (2 C), 128.6 (2 C), 128.9, 129.0, 131.2, 131.6 (2 C), 166.9.

Example 17

Preparation of Mixed Blend Monoesters of Methylbiphenyl Carboxylic Acids+Oxo Alcohols (NGP62)

The following three monoesters were combined: 4-methylbiphenyl-4-oxoC$_9$ ester (exmple 8) (17.62 g), 2-methylbiphenyl-3-oxoC$_{10}$ ester (example 10) (3.86 g), and 4-methybiphenyl-2-oxoC$_9$ ester (example 9) (3.95 g).

Example 18

Esterification of 2,2'-biphenyl dicarboxylic acid with C$_5$ alcohols (65/35, 1-pentanol/2-methyl-1-butanol NGP 51)

Into a 4-necked 500 ml round bottom flask equipped with an air stirrer, thermometer, N$_2$ inductor, Dean-Stark trap and chilled water cooled condenser were added 2,2'-biphenyl dicarboxylic acid (100 g, 0.46 mole), and mixed C$_5$ alcohols (65/35, 1-pentanol/2-methyl-1-butanol) (165.0 g, 1.875 mole) to approximate the component distribution of an OXO-C$_5$ alcohol. The reaction mixture was heated for a total of 73 hours at 137-169° C. with GC sampling. The product was concentrated using a Claisen adapter, chilled water cooled condenser and receiving flask. The concentrated product was dissolved in an equal weight of toluene (140 g) and was washed twice with 50 g of a 3 wt % sodium hydroxide solution followed by distilled water (50 g). The upper toluene phase was then dried over magnesium sulfate, filtered and distilled. The diester distilled at Bp=174-184° C./0.10 mm. The purity obtained by GC analysis was 99.1%. The distillate was clear yellow liquid and was treated with decolorizing charcoal with stirring at room temperature for 2 hours. The product was filtered twice to remove all the charcoal. Clear and colorless sample was obtained.

Example 19

Esterification of 2,2'-biphenyl dicarboxylic acid with C$_6$ alcohols (65/35, 1-hexanol/2-methyl-1-pentanol NGP-53)

Into a 4-necked 500 ml round bottom flask equipped with an air stiffer, thermometer, N$_2$ inductor, Dean-Stark trap and chilled water cooled condenser were added 2,2'-biphenyl dicarboxylic acid (199.3 g, 0.823 mole), and C$_6$ alcohols (65/35, 1-hexanol/2-methyl-1-pentanol) (336.2 g, 3.2903 mole) to approximate the component distribution of an OXO-C$_6$ alcohol. The reaction mixture was heated a total of 24 hours at 150-155° C. with GC sampling. The product was concentrated using a Claisen adapter, chilled water cooled condenser and receiving flask. The concentrated product was dissolved in an equal weight of toluene (347 g) and was washed twice with 100 g of a 3 wt % sodium hydroxide solution followed by distilled water (100 g). The upper toluene phase was then dried over magnesium sulfate, filtered and distilled. The diester distilled at Bp=189-191° C./0.10 mm. The distillates were clear yellow liquids and were dissolved in toluene then treated with decolorizing charcoal with stirring at room temperature for 2 hours. The product was filtered twice to remove all the charcoal then distilled overhead. A clear off white liquid was obtained Bp=184° C./0.10 mm with a purity of 97.9% (by GC).

Example 20

Esterification of 2,2'-biphenyl dicarboxylic acid with Oxo C9 alcohols (NGP 73)

Into a 4-necked 500 ml round bottom flask equipped with an air stirrer, thermometer, N$_2$ inductor, Dean-Stark trap and chilled water cooled condenser were added 2,2'-biphenyl dicarboxylic acid (54.4 g, 0.252 mole), and OXO-C$_9$ alcohols (145.4 g, 1.01 mole) and xylenes (50 g, 0.47 mole). The reaction mixture was heated a total of 24 hours at 172-189° C. with GC sampling. The product was concentrated using a Claisen adapter, chilled water cooled condenser and receiving flask. The concentrated product was dissolved in an equal weight of toluene (99.7 g) and was washed three times with 50 g of a 3 wt % sodium hydroxide solution followed by distilled water (50 g) twice. The upper toluene phase was then dried over magnesium sulfite, filtered and distilled. The diester distilled at Bp=237° C./0.25-0.30 mm. The distillates were clear yellow orange liquids and were distilled a second time at 206-215° C./0.22-0.16 mm vacuum. The distillate remained yellow so it was dissolved in toluene then treated with decolorizing charcoal with stirring at room temperature for 2 hours. The product was filtered twice to remove all the charcoal. A clear light yellow liquid was obtained with a purity of 99.4% by GC.

Example 21

Preparation of dihexylbiphenyl 4,4'dicarboxylate using linear -C$_6$ alcohols (NGP-78): Hexyl 4-bromobenzoate was Prepared from the Condensation of 4-bromobenzoic acid and Hexanol by Refluxing in Benzene with Water Removal via a Dean-Stark Trap. The Ester was Purified by Distillation Under N$_2$, hexyl 4-bromobenzoate (1 equiv), bispinacolatodiboron (0.5 equiv), potassium carbonate (3 equiv) and PdCl$_2$dppf (0.02 equiv) were dissolved in DMSO to make a 0.15 M solution with respect to the bromobenzoic ester. The solution was degassed with N$_2$, then heated at 80° C. overnight. Water and ethyl acetate were then added to the cooled reaction and the layers separated. The organic layer was extracted with ethyl acetate, then the combined organic layers washed with 10% HCl, water and brine. It was then dried (MgSO$_4$), filtered and concentrated. The crude oil was purified by passage through a short silica gel column (eluting with 10:90 acetone:petroleum ether) and vacuum distillation.

Example 22

Preparation of dihexyl biphenyl-3,3'-dicarboxylate using OXO-C$_6$ alcohols (NGP-82)

Hexyl 3-bromobenzoate was prepared from the condensation of 3-bromobenzoic acid and OXO hexanol by refluxing in benzene with water removal via a Dean-Stark trap. The ester was purified by distillation: $^1$H NMR (400 MHz, CDCl$_3$) δ 0.90 (m, 3 H), 1.34 (m, 6 H), 1.76 (m, 2 H), 4.31 (t, J=6.6 Hz, 2 H), 7.30 (t, J=8.0 Hz, 1 H), 7.65 (m, 1 H), 7.95 (m, 1 H), 8.16 (s, 1 H); $^{13}$C NMR (100 MHz, CDCl$_3$) 14.1, 22.6, 25.8, 28.8, 31.6, 65.7, 122.6, 128.2, 130.0, 132.6, 132.7, 135.9, 165.4. Under N$_2$, hexyl 3-bromobenzoate (1 equiv), bispinacolatodiboron (0.5 equiv), potassium carbonate (3 equiv) and PdCl$_2$dppf (0.02 equiv) were dissolved in DMSO to make a 0.15 M solution with respect to the bromobenzoic ester. The solution was degassed with N$_2$, then heated at 80° C. overnight. Water and ethyl acetate were then added to the cooled reaction and the layers separated. The organic layer was extracted with ethyl acetate, then the combined organic layers washed with 10% HCl, water and brine. it was then dried (MgSO$_4$), filtered and concentrated. The crude oil was purified by passage through a short silica gel column (eluting with 10:90 acetone:petroleum ether) and vacuum distillation: $^1$H NMR (400 MHz, CDCl$_3$) δ 0.91 (m, 6 H), 1.36 (m, 12 H), 1.80 (m, 4 H), 4.36 (t, J=6.6 Hz, 2 H), 7.54 (m, 2 H), 7.81 (m, 2 H), 8.06 (d, J=8.0 Hz, 2 H), 8.30 (s, 2 H); $^{13}$C NMR (100 MHz, CDCl$_3$) 14.2 (2 C), 22.7 (2 C), 25.9 (2 C), 28.9 (2 C), 31.6 (2 C), 65.5 (2 C), 128.4-131 (8 C), 140.6 (4 C), 166.6 (2 C).

Example 23

Preparation of dihexyl biphenyl-3,4'-dicarboxylate using Oxo C$_6$ alcohols (NGP-97)

Hexyl 4-bromobenzoate was prepared from the condensation of 4-bromobenzoic acid and OXO-C$_6$ alcohols by relaxing in benzene with water removal via a Dean-Stark trap, then purified by distillation: $^1$H NMR (400 MHz, CDCl$_3$) δ 0.86-1.76 (m, 13 H), 4.31 (m, 2 H), 7.58 (d, J=8 Hz, 2 H), 7.91 (d, J=8.0 Hz, 2 H). Hexyl 3-bromobenzoate was prepared from the condensation of 3-bromobenzoic acid and OXO-C$_6$ alcohols by refluxing in benzene with water removal via a Dean-Stark trap, then purified by distillation: $^1$H NMR (400 MHz, CDCl$_3$) δ 0.91-1.77 (m, 11 H), 4.34 (m, 2 H), 7.31 (m, 2 H), 7.64 (m, 1 H), 7.77 (d, J=8.0 Hz, 1 H). Hexyl 4-bromobenzoate (1 equiv), bispinacolatodiboron (1.1 equiv) and potassium acetate (3 equiv) were dissolved in DMF to make a 0.25 M solution with respect to the bromobenzoic ester. The mixture was degassed with N$_2$ and palladium diacetate (0.02 equiv) was added. The reaction was heated between 80-90° C. until completion (approx. 5 h), then cooled. Water was added and the mixture extracted 3 times with ethyl acetate. The combined organic layers were washed twice with water and twice with brine, then dried (MgSO4), filtered and concentrated under reduced pressure. The unpurified grayish yellow oil was then transferred to a 3-neck flask and dissolved in toluene to make a 0.2 M solution. An equivalent of a hexyl 3-bromobenzoate and a 2 M solution of potassium carbonate (5 equiv) was added and the mixture degassed. Palladium tetrakistriphenylphosphine (0.01 equiv) was added and the reaction heated at reflux overnight. After cooling, the aqueous layer was extracted with ethyl acetate and combined organic layers washed twice with water and twice with brine. It was then dried (MgSO$_4$), filtered and concentrated. The crude oil was purified by passage through a short silica gel column (eluting with 10:90 ethyl acetate:hexanes) followed by vacuum distillation: $^1$H NMR (400 MHz, CDCl$_3$) δ 0.90-1.79 (m, 25 H), 4.32 (m, 2 H), 7.52 (t, J=8.0 Hz, 1 H), 7.67 (d, J=8.0 Hz, 2 H), 7.77 (m, 1 H), 8.03 (m, 1 H), 8.11 (m, 2 H), 8.28 (s, 1 H); $^{13}$C NMR (100 MHz, CDCl$_3$) 11.4-35.9 (10 C), 63.69, 65.4, 127.2 (2C), 128.5, 129.2, 129.3, 129.9, 130.3 (2 C), 131.5, 131.6, 140.5, 144.6, 166.6 (2 C).

Example 24

Preparation of 2,3'-biphenylcarboxylate using Oxo C$_6$ alcohols (NGP-98)

Hexyl 2-bromohenzoate was prepared from the condensation of 2-bromobenzoic acid and OXO-C$_6$ alcohols by refluxing in benzene with water removal via a Dean-Stark trap, then purified by distillation: $_1$H NMR (400 MHz, CDCl$_3$) δ 0.91-1.77 (m, 11 H), 4.34 (m, 2 H), 7.31 (m, 2 H), 7.64 (d, J=8.0 Hz, 1 H), 7.77 (d, J=8.0 Hz, 1H). Hexyl 3-bromobenzoate (1 equiv), bispinacolatodiboron (1.1 equiv) and potassium acetate (3 equiv) were dissolved in DMF to make a 0.25 M solution with respect to the bromobenzoic ester. The mixture was degassed with N$_2$ and palladium diacetate (0.02 equiv) was added. The reaction was heated between 80-90° C. until completion (approx. 5 h), then cooled. Water was added and the mixture extracted 3 times with ethyl acetate. The combined organic layers were washed twice with water and twice with brine, then dried (MgSO4), filtered and concentrated under reduced pressure. The unpurified grayish yellow oil was then transferred to a 3-neck flask and dissolved in toluene to make a 0.2 M solution. An equivalent of a hexyl 2-bromobenzoate and a 2 M solution of potassium carbonate (5 equiv) was added and the mixture degassed. Palladium tetrakistriphenylphosphine (0.01 equiv) was added and the reaction heated at reflux overnight. After cooling, the aqueous layer was extracted with ethyl acetate and combined organic layers washed twice with water and twice with brine. It was then dried (MgSO$_4$), filtered and concentrated. The crude oil was purified by passage through a short silica gel column (eluting with 10:90 ethyl acetate:hexanes) followed by vacuum distillation: $^1$H NMR (400 MHz, CDCl$_3$) δ 0.81-1.77 (m, 25 H), 4.04 (m, 2 H), 4.33 (m, 2 H), 7.46 (m, 1 H), 7.50 (m, 4 H), 7.89 (m, 1 H), 8.03 (m, 2 H); $^{13}$C NMR (100 MHz, CDCl$_3$) 14.9-35.4 (10 C), 63.7, 65.4, 127.8, 128.2, 128.5, 129.6, 130.3, 130.7, 130.9, 131.2, 131.5, 133.0, 141.7, 142.1, 166.6, 168.6.

Table 2 summarizes the conditions for forming different esters.

TABLE 2

| Example # | Acid | Alcohol | Temp ° C. | Purity, % By GC |
|---|---|---|---|---|
| 1 | 4-phenyl benzoic acid | OXO-C$_{10}$ | 208-220 | 99.5 |
| 2 | 4-phenyl benzoic acid | OXO-C$_9$ | 185-220 | 99.5 |
| 3 | 3-phenyl benzoic acid | OXO-C$_{10}$ | 175-183 | 99.2 |
| 4 | 2-phenyl benzoic acid | OXO-C$_9$ | 205-208 | 99.6 |
| 5 | Blend of example 1, 3 and 4 | | | |
| 6 | 4-cyclohexylbenzoic acid | OXO-C$_{10}$ | 217-220 | 99.2 |
| 7a | blend of biphenyl-4-carboxylic acid (70%) plus 4-cyclohexylbenzoic acid (30%),2'-methylbiphenyl-3-carboxylic acid | OXO-C$_{10}$ | 145-182 | 99.42 |

TABLE 2-continued

| Example # | Acid | Alcohol | Temp °C. | Purity, % By GC |
|---|---|---|---|---|
| 7b | blend of biphenyl-4-carboxylic acid (70%) plus 4-cyclohexylbenzoic acid (30%), | OXO-C$_{10}$ | 208-220 | 99.6 |
| 7c | blend of biphenyl-4-carboxylic acid (50%) plus 4-cyclohexylbenzoic acid (50%), | OXO-C$_{10}$ | 208-220 | 99.6 |
| 7d | blend of biphenyl-4-carboxylic acid (30%) plus 4-cyclohexylbenzoic acid (70%), | OXO-C$_{10}$ | 208-220 | 99.6 |
| 8 | 4'-methylbiphenyl-4-carboxylic acid | OXO-C9 | 184-185 | 99.6 |
| 9 | 4'-methylbiphenyl-2-carboxylic acid | OXO-C9 | 145-162 | 99.86 |
| 10 | 2'-methylbiphenyl-3-carboxylic acid | OXO-C$_{10}$ | 175-182 | 99.42 |
| 11 | 4'-methylbiphenyl-3-carboxylic acid | OXO-C$_{10}$ | | |
| 12 | 2'-methyl-3-biphenylcarboxylic acid | OXO-C$_{10}$ | | |
| 13 | 3'-methyl-4-biphenylcarboxylic acid | OXO-C$_{10}$ | | |
| 14 | 3'-methyl-4-biphenylcarboxylic acid | OXO-C9 | | |
| 15 | 3'-methy-2-biphenylcarboxylic acid | OXO-C$_{10}$ | | |
| 16 | 3'-methyl-3-biphenylcarboxylic acid | OXO-C$_{10}$ | | |
| 17 | blend of examples 8, 9, & 10 | OXO-C9 + OXO-C10 | NA | NA |
| 18 | biphenyl-2,2'-dicarboxylic acid | C$_5$ (65/35) n-pentanol/2- | 174-184 | 99.1 |
| 19 | biphenyl-2,2'-dicarboxylic acid | C$_6$ (65/35) n-hexanol/2-methylpentanol | 189-191 | 97.9 |
| 20 | biphenyl-2,2'-dicarboxylic acid | OXO-C9 | 206-215 | 99.4 |
| 21 | biphenyl-4,4'-dicarboxylic acid | Linear C6 alcohol | | |
| 22 | biphenyl-4,4'-dicarboxylic acid | OXO-C6 | | |
| 23 | biphenyl-3,4'-dicarboxylic acid | OXO-C6 | | |
| 24 | biphenyl-2,3'-dicarboxylic acid | OXO-C6 | | |

The structures of the samples listed in the above table are shown below:

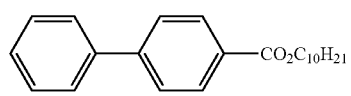

Example 1

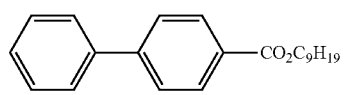

Example 2

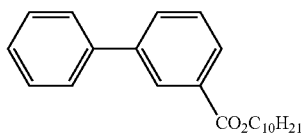

Example 3

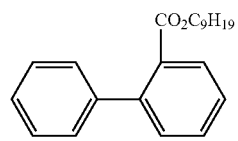

Example 4

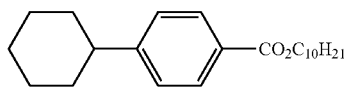

Example 6

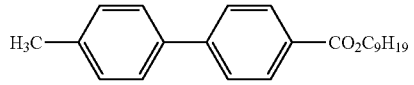

Example 8

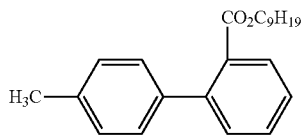

Example 9

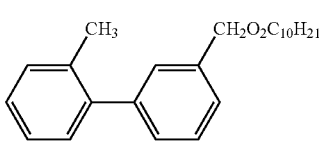

Example 10

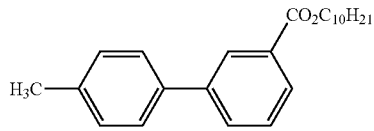

Example 11

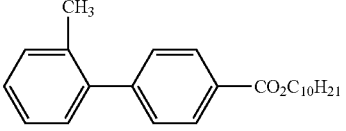

Example 12

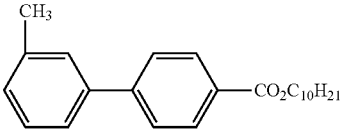

Example 13

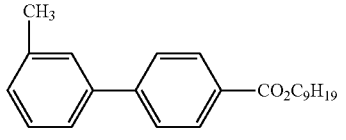

Example 14

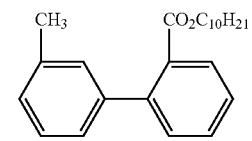

Example 15

Example 16

-continued

Example 18
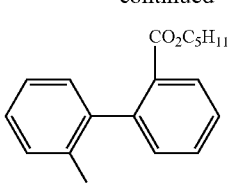

Example 19
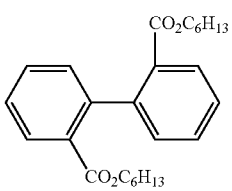

Example 20
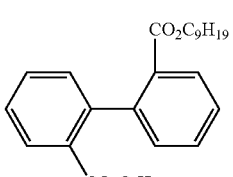

Example 21
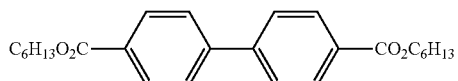

Example 22

Example 23
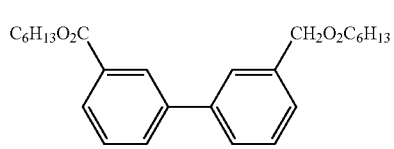

Example 24
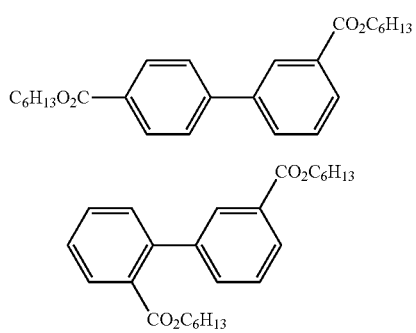

Method for Preparation of Plasticized Polymer Testing Bars by Solvent Method A:

A 5.85 g portion of the ester sample (or comparative commercial plasticizer DINP) was weighed into an Erlenmeyer flask which had previously been rinsed with uninhibited tetrahydrofuran (THF) to remove dust. A 0.82 g portion of a 70:30 by weight solid mixture of powdered Drapee® 6.8 (Crompton Corp.) and Mark® 4716 (Chemtura USA Corp.) stabilizers was added along with a stirbar. The solids were dissolved in 117 mL uninhibited THF. Oxy Vinyls® 240F PVC (11.7 g) was added in powdered form and the contents of the flask were stirred overnight at room temperature until dissolution of the PVC was complete. The clear solution was poured evenly into a flat aluminum paint can lid (previously rinsed with inhibitor-free THF to remove dust) of dimensions 7.5" diameter and 0.5" depth. The lid was placed into an oven at 60° C. for 2 hours with a moderate nitrogen purge. The pan was removed from the oven and allowed to cool for a ~5 min period. The resultant clear film was carefully peeled of of the aluminum, flipped over, and placed back evenly into the pan. The pan was then placed in a vacuum oven at 70° C. overnight to remove residual THF. The dry, flexible, typically almost colorless film was carefully peeled away and exhibited no oiliness or inhomogeneity unless otherwise noted. The film was cut into small pieces to be used for preparation of test bars by compression molding (size of pieces was similar to the hole dimensions of the mold plate). The film pieces were stacked into the holes of a multi-hole steel mold plate, preheated to 170° C., having hole dimensions 20 mm×12.8 mm×1.8 mm (ASTM D1693-95 dimensions). The mold plate was pressed in a PHI company QL-433-6-M2 model hydraulic press equipped with separate heating and cooling platforms. The upper and lower press plates were covered in Teflon™-coated aluminum foil and the following multistage press procedure was used at 170° C. with no release between stages: (1) 3 minutes with 1-2 ton overpressure; (2) 1 minute at 10 tons; (3) 1 minute at 20 tons; (4) 1 minute at 30 tons; (5) 3 additional minutes at 30 tons; (6) release and 3 minutes in the cooling stage of the press (7° C.) at 30 tons. A knockout tool was then used to remove the sample bars with minimal flexion. Typically near-colorless, flexible bars were obtained which, when stored at room temperature, showed no oiliness or exudation after pressing unless otherwise noted. The bars were allowed to age at room temperature for at least 1 week prior to evaluation of phase behavior with Differential Scanning Calorimetry (DSC) and thermo-physical properties with Dynamic Mechanical Thermal Analysis (DMTA).

Method for Preparation of Plasticized Polymer Testing Bars by Melt Mixing Method B:

In a 250 ml beaker is added 2.7 g of an additive package containing a 70/30 wt/wt of Paraplex G62 ESO/Mark 4716. To this is added 19.1 g of plasticizer and the mixture is stirred with a spatula until blended. After blending, 38.2 g of PVC is added and the mixture is mixed forming a paste. The mixture is added to the melt mixture. A Haake Rheomix 600 mixer manufactured by Haake PolyLab System is preheated to the desired mixing temperature (165° C. for most experiments). A coarsely mixed sample consisting of plasticizer, polyvinylchloride and stabilizers is added to the mixer while stirring at 35 rpm. After addition the mixer is stopped for one minute. The mixer is started again and the sample is mixed for five minutes. After mixing for five minutes the mixer is stopped and disassembled. The mixed sample is removed hot.

98° C. Weight Loss Comparison of PVC Bars Plasticized with Esters Versus PVC Bars Plasticized with Commercial Plasticizer:

Two each of the PVC sample bars prepared above were placed separately in aluminum weighing pans and placed inside a convection oven at 98° C. Initial weight measurements of the hot bars and measurements taken at specified time intervals were recorded and results were averaged between the bars. The averaged results are shown in Table 5. Notes on the appearance and flexibility of the bars at the end of the test are also given.

70° C. Humid Aging Clarity Comparison of PVC Bars Plasticized with Esters Versus PVC Bars Plasticized with Commercial Plasticizer.

Using a standard one-hole office paper hole punch, holes were punched in two each of the sample bars prepared above ⅛" from one end of the bar. The bars were hung in a glass pint jar (2 bars per jar) fitted with a copper insert providing a stand and hook. The jar was filled with ~½" of distilled water and the copper insert was adjusted so that the bottom of each bar was ~1" above the water level. The jar was sealed, placed in a 70° C. convection oven, and further sealed by winding Teflon™ tape around the edge of the lid. After 21 days the jars were removed from the oven, allowed to cool for ~20 minutes, opened, and the removed bars were allowed to sit under ambient conditions in aluminum pans (with the bars propped at an angle to allow air flow on both faces) or hanging from the copper inserts for 14 days (until reversible humidity-induced opacity had disappeared). The bars were evaluated visually for clarity. All bars exhibited complete opacity during the duration of the test and for several days after removal from the oven. Results are shown in Table 6. Notes on the appearance and flexibility of the bars at the end of the test are also given.

TABLE 6

70° C. Humid Aging Clarity and Appearance properties of Ester- and DINP-Containing PVC Bars.

| Example No. (Ester Used in Bar) | Notes on Bar |
| --- | --- |
| DINP[(1)] | Flex and brownish |
| 1 | Similar to DINP |
| 2 | Very flex and clear |
| 3 | Very flex and colorless |
| 4 | Very flex and yellowish |
| 5 | Very flex and yellowish |
| 6 | Very flex and yellowish |
| 7a | More flex than DINP |
| 7b | More flex than DINP |
| 7c | Much more flex than DINP |
| 7d | Much more flex than DINP |
| 8 | NA |
| 9 | NA |
| 10 | Stiffer than DINP |
| 11 | NA |
| 12 | NA |
| 13 | NA |
| 14 | NA |
| 15 | Similar to DINP |
| 16 | A bit stiffer than DINP, similar color to DINP |
| 17 | Similar to DINP |
| 18 | Colorless and flex |
| 19 | Similar to DINP |
| 20 | Very stiff |
| 21 | NA |
| 77 | More flex than DINP |
| 23 | Similar to DINP |
| 24 | Similar to DINP |

[(1)]Bars made following example 44 method A
[(2)]Bars made following example 44 method B Differential Scanning Calorimetry (DSC) and Thermogravimetric Analysis (TGA) Property Study of Esters and Plasticized Bars:

Thermogravimetric Analysis (TGA) was conducted on the neat esters using a TA Instruments TGA5000 instrument (25-450° C., 10° C./min, under 25 cc $N_2$/min flow through furnace and 10 cc $N_2$/min flow through balance; sample size approximately 10 mg). Table 4 provides comparisons of volatilities and glass transitions (Tg) of the different ester fractions. Tgs given in Table 4 are midpoints of the second heats obtained by Differential Scanning Calorimetry (DSC) using a TA Instruments Q2000 calorimeter fitted with a liquid $N_2$ cooling accessory. Samples were loaded at room temperature and cooled to −130° C. at 10° C./min and analyzed on heating to 75° C. at a rate of 10° C./min. Table 5 provides a volatility comparison of the neat and plasticized PVC bars.

TABLE 4

| Example | TGA 1% Wt Loss (° C.) | TGA 5% Wt Loss (° C.) | TGA 10% Wt Loss (° C.) | TGA Wt Loss at 220° C. (%) | DSC $T_g$ (° C.) |
| --- | --- | --- | --- | --- | --- |
| 1 | 182.5 | 214.3 | 231.9 | 6.3 | −64.7 |
| 2 | 177.3 | 207 | 221.9 | 9.2 | −64.1 |
| 3 | 171.1 | 200.1 | 215.3 | 12.2 | −66.7 |
| 4 | 150.5 | 179.8 | 194.5 | 28.1 | −66.3 |
| 5 | 161.5 | 191.8 | 207.6 | 16.5 | −66.3 |
| 6 | 167.7 | 199.0 | 215.1 | 12.2 | −75.2 |
| 7a | 170.8 | 200.3 | 216.4 | 11.5 | −68.0 |
| 7b | 176.2 | 206.0 | 221.1 | 9.5 | −69.2 |
| 7c | 173.3 | 203.0 | 217.9 | 11.0 | −71.3 |
| 7d | 172.5 | 201.6 | 216.3 | 11.8 | −73.2 |
| 8 | 183.7 | 219.2 | 235.3 | 5.2 | −80.6 |
| 9 | 173.9 | 204.8 | 220.2 | 9.9 | −73.6 |
| 10 | 171.8 | 203.7 | 219.9 | 10.1 | −65.9 |
| 11 | 188.6 | 219.4 | 235.3 | 5.1 | −63.2 |
| 12 | 187.9 | 214.1 | 229.8 | 6.6 | −63.9 |
| 13 | 192.1 | 222.9 | 238.7 | 4.4 | −65.9 |
| 14 | 185.3 | 216.4 | 232.1 | 5.9 | −64.1 |
| 15 | 148.6 | 180.9 | 196.3 | 26.1 | −67.7 |
| 16 | 177.1 | 208.6 | 225.5 | 8.6 | −66.9 |
| 17 | 173.1 | 208.2 | 224.6 | 8.2 | −63.3 |
| 18 | 159.9 | 188.6 | 203.1 | 19.8 | −75.0 |
| 19 | 173.9 | 204.8 | 220.2 | 9.9 | −73.6 |
| 20 | 166.1 | 192.8 | 206.4 | 18.7 | −76.0 |
| 21 | — | — | — | — | — |
| 22 | — | — | — | — | — |
| 23 | 216.06 | 249.13 | 265.1 | 1.195 | −64.0 |
| 24 | — | — | — | — | — |

— Data not taken

TABLE 5

| Plasticizer Used in Bar | TGA 1% Wt Loss (° C.) | TGA 5% Wt Loss (° C.) | TGA 10% Wt Loss (° C.) | TGA % Wt Loss at 220 (° C.) |
| --- | --- | --- | --- | --- |
| None (Neat PVC) | 129.9 | 192.3 | 255.4 | 6.3 |
| 1 | 199.1 | 239.9 | 251.7 | 2.3 |
| 2 | 192.5 | 232.4 | 251.2 | 3.1 |
| 3 | 188.0 | 230.2 | 246.8 | 3.43 |
| 4 | 170.9 | 207.4 | 239.7 | 6.7 |
| 5 | 180.4 | 222.7 | 243.6 | 4.6 |
| 6 | 185.3 | 226.9 | 244.7 | 3.9 |
| 7a | 191.1 | 233.0 | 246.0 | 3.1 |
| 7b | 188.3 | 229.0 | 244.7 | 3.6 |
| 7c | 188.8 | 230.2 | 245.6 | 3.4 |
| 7d | 186.5 | 226.8 | 244.2 | 3.9 |
| 8 | 206.1 | 244.2 | 257.1 | 1.8 |
| 9 | 176.2 | 214.7 | 243.2 | 5.9 |
| 10 | 189.0 | 230.2 | 247.9 | 3.5 |
| 11 | 194.7 | 235.9 | 248.2 | 2.7 |
| 12 | 187.3 | 229.5 | 245.1 | 3.5 |
| 13 | 196.5 | 238.7 | 249.3 | 2.4 |
| 14 | 192.1 | 235.1 | 246.7 | 2.7 |
| 15 | 169.0 | 210.2 | 235.2 | 6.7 |
| 16 | 191.5 | 234.8 | 246.1 | 2.9 |
| 17 | 191.2 | 237.6 | 252.1 | 2.8 |
| 18 | 184.3 | 225.2 | 249.2 | 4.2 |
| 19 | 188.5 | 231.9 | 247.4 | 3.3 |
| 20 | 218.7 | 249.1 | 262.4 | 1.1 |
| 21 | 233.0 | 245.6 | 254.6 | 0.7 |
| 22 | 217.3 | 250.9 | 265.5 | 1.1 |
| 23 | 229.6 | 251.7 | 265.0 | 0.8 |
| 24 | 202.3 | 243.9 | 253.3 | 1.8 |

Demonstration of Plasticization of PVC with Different Esters Made Using this Disclosure via Differential Scanning Calorimetry (DSC):

Differential Scanning Calorimetry (DSC) was performed on the compression-molded sample bars prepared above (PVC:plasticizer ratio=2:1) using a TA Instruments Q2000 calorimeter fitted with a liquid $N_2$ cooling accessory. Samples were loaded at room temperature and cooled to −110° C. at 10° C./min, and then analyzed on heating at a rate of 10° C./min to 130-160° C. for plasticized PVC bars, and to 100° C. for the comparative neat PVC bar. Small portions of the sample bars (typical sample mass 5-7 mg) were cut for analysis, making only vertical cuts perpendicular to the largest surface of the bar to preserve the upper and lower compression molding "skins". The pieces were then placed in the DSC pans so that the upper and lower "skin" surfaces contacted the bottom and top of the pan. Table 6 provides the first heat Tg onset, midpoint, and end for neat PVC and the plasticized bars. A lowering and broadening of the glass transition for neat PVC is observed upon addition of the esters, indicating plasticization and extension of the flexible temperature range of use for neat PVC.

TABLE 6

| Plasticizer Used in Bar | $T_g$ Onset (° C.) | $T_g$ Midpt (° C.) | $T_g$ End (° C.) | $T_m$ Max (° C.) and $DH_f$ (J/g)$^a$ |
|---|---|---|---|---|
| None (Neat PVC) | 44.5 | 46.4 | 48.9 | not calc. |
| 1 | −35.3 | −12.6 | 10.2 | 61.6, 1.4 |
| 2 | −18.1 | −1.1 | 16.1 | 55.3, 0.9 |
| 3 | −39.5 | −15.6 | 8.1 | 55.2, 1.1 |
| 4 | −42.7 | −18.9 | 4.9 | 60.1, 0.5 |
| 5 | −37.9 | −13.8 | 10.4 | 55.2, 0.9 |
| 6 | −39.0 | −14.0 | 12.5 | 58.2, 0.9 |
| 7a | −32.7 | −10.6 | 11.5 | 54.1, 1.0 |
| 7b | −30.4 | −9.1 | 12.3 | 56.4, 1.1 |
| 7c | −33.3 | −10.6 | 12.4 | 56.3, 1.0 |
| 7d | −36.1 | −13.4 | 10.0 | 55.5, 1.1 |
| 8 | −17.2 | −1.3 | 14.6 | 54.5, 0.3 |
| 9 | −27.0 | −10.6 | 6.0 | 54.7, 86.1 and 0.5, 0.2, respectively |
| 10 | −39.4 | −11.9 | 15.9 | 53.0, 1.1 |
| 11 | −28.5 | −8.0 | 12.7 | 52.3, 1.1 |
| 12 | −65.5, −33.5 | −61.3, −11.1 | −57.0, 11.7 | 55.2, 0.9 |
| 13 | −25.5 | −6.0 | 13.5 | 56.9, 0.9 |
| 14 | −24.6 | −4.6 | 15.4 | 56.0, 1.0 |
| 15 | −36.6 | −13.3 | 10.7 | 54.6, 0.8 |
| 16 | −28.7 | −8.7 | 11.6 | 54.5, 0.8 |
| 17 | −33.8 | −13 | 8.3 | 55.1, 0.9 |
| 18 | −15.9 | −0.5 | 14.8 | 56.2, 0.8 |
| 19 | −19.6 | −3.6 | 12.4 | 56.7, 0.9 |
| 20 | −18.5 | −8.8 | 0.9 | 54.6, 1.1 |
| 21. | −2.5 | 8.2 | 21.2 | — |
| 22 | −31.0 | 10.2 | 10.6 | 53.5, 0.8 |
| 23 | −19.2 | −2.2 | 15.0 | 53.9, 0.8 |
| 24 | −22.9 | −8.2 | 6.9 | 58.2, 1.0 |

— Data not obtained.
$^a$Most sample bars showed a weak melting point ($T_m$) from the crystalline portion of PVC. Often this weak transition was not specifically analyzed, but data is given here in instances where it was recorded, Demonstration of Plasticization of PVC with Different Esters via Dynamic Mechanical Thermal Analysis (DMTA):

A TA Instruments DMA Q800 fitted with a liquid $N_2$ cooling accessory and a three-point bend clamp assembly was used to measure the thermo-mechanical performance of neat PVC and the PVC/plasticizer blend sample bars prepared above. Samples were loaded at room temperature and cooled to −90° C. at a cooling rate of 3° C./min. After equilibration, a dynamic experiment was performed at one frequency using the following conditions: 3° C./min heating rate, 1 Hz frequency, 20 μm amplitude, 0.01 N pre-load force, force track 120%. Two or three bars of each sample were typically analyzed and numerical data was averaged. The DMTA measurement gives storage modulus (elastic response modulus) and loss modulus (viscous response modulus); the ratio of loss to storage moduli at a given temperature is tan delta. The beginning (onset) of the glass transition, Tg (temperature of brittle-ductile transition) was obtained for each sample by extrapolating a tangent from the steep inflection of the tan delta curve and the first deviation of linearity from the baseline prior to the beginning of the peak. Table 7 provides a number of DMTA parameters for neat PVC and PVC bars plasticized with materials described above: Tg onset (taken from tan delta); peak of the tan delta curve; storage modulus at 25° C.; and the temperature at which the storage modulus equals 100 MPa (this temperature was chosen to provide an arbitrary measure of the temperature at which the PVC loses a set amount of rigidity; too much loss of rigidity may lead to processing complications for the PVC material.). The storage modulus at 25° C. provides an indication of plasticizer efficiency (i.e., the amount of plasticizer required to achieve a specific stiffness); the higher the storage modulus, the more plasticizer required. The flexible use temperature range of the plasticized PVC samples is evaluated as the range between the Tg onset and the temperature at which the storage modulus was 100 MPa. A lowering and broadening of the glass transition for neat PVC is observed upon addition of the esters, indicating plasticization and extension of the flexible temperature range of use for neat PVC. Plasticization (enhanced flexibility) is also demonstrated by lowering of the PVC room temperature storage modulus upon addition of the esters.

TABLE 7

| Plasticizer Used in Bar | Tan δ $T_g$ Onset (° C.) | Tan δ Peak (° C.) | 25° C. Storage Mod. (MPa) | Temp. of 100 MPa Storage Mod. (° C.) | Flexible Use Range (° C.)$^a$ |
|---|---|---|---|---|---|
| None (Neat PVC) | 44.0 | 61.1 | 1433 | 57.1 | 13.1 |
| 1 | −38.6 | 20.6 | 36.4 | 17.3 | 55.9 |
| 2 | −28.3 | 19 | 35.7 | 17.1 | 45.4 |
| 3 | −40.3 | 14.5 | 35.4 | 14.4 | 54.8 |
| 4 | −34.8 | 20.2 | 48.5 | 19.1 | 53.9 |
| 5 | −37.0 | 16.3 | 26.6 | 13.5 | 50.5 |
| 6 | −50.0 | 26.8 | 59.9 | 20.0 | 70.0 |
| 7a | −34.7 | 23.1 | 35.0 | 16.9 | 51.5 |
| 7b | −38.2 | 20.3 | 42.5 | 16.5 | 54.7 |
| 7c | −42.7 | 19.5 | 58.2 | 18.2 | 60.9 |
| 7d | −43.2 | 23.2 | 49.3 | 18.2 | 61.4 |
| 8 | −20.5 | 23.4 | 52.4 | 20.5 | 41.0 |
| 9 | −31.6 | 17.1 | 38.9 | 16.5 | 48.2 |
| 10 | −45.2 | 23.1 | 49.1 | 18.4 | 63.6 |
| 11 | −33.6 | 21.0 | 31.6 | 16.2 | 49.8 |
| 12 | −40.9 | 27.1 | 66.3 | 21.4 | 62.4 |
| 13 | −32.6 | 19.9 | 38.9 | 16.7 | 49.3 |
| 14 | −27.0 | 20.4 | 38.4 | 16.8 | 43.8 |
| 15 | −40.2 | 18.2 | 34.3 | 13.8 | 54.0 |
| 16 | −38.0 | 17.8 | 34.6 | 14.7 | 52.6 |
| 17 | −24.8 | 20.4 | 45.0 | 18.1 | 42.9 |
| 18 | −26.7 | 21.0 | 37.5 | 17.5 | 44.2 |
| 19 | −24.0 | 17.6 | 42.8 | 17.2 | 41.2 |
| 20 | −28.1 | 24.5 | 61.3 | 20.6 | 48.7 |
| 21 | 18.2 | 47.1 | 1588 | 43.6 | 25.5 |
| 22 | −24.9 | 20.7 | 37.4 | 16.7 | 41.6 |
| 23 | −21.3 | 21.9 | 56.9 | 20.1 | 41.4 |
| 24 | −27.4 | 18.9 | 35.8 | 12.0 | 39.4 |

Table 8 summarizes the critical tests for plasticizing performance using esters from Examples 1-10; DINP (diisononylphthalate) is used for comparison.

TABLE 8

| Example No. (Ester Used in Bar) | Viscosity (units) | Tg | Notes on films or bars |
|---|---|---|---|
| DINP[1] | 100 | −79 | |
| 1 | 134 | −64.7 | Flex and colorless similar to DINP |
| 2 | NA | −64.1 | Flex and colorless similar to DINP |
| 3 | 133 | −75.0 | Flex and colorless similar to DINP |

TABLE 8-continued

| Example No. (Ester Used in Bar) | Viscosity (units) | Tg | Notes on films or bars |
|---|---|---|---|
| 4 | NA | −66.3 | Stiffer than DINP |
| 5 | NA | −80.6 | Very flexable |
| 6 | 104 | −60.4 | Flex, a bit darker than DINP |
| 7a | NA | | Similar to DINP |
| 7b | NA | −75.1 | Similar to DINP |
| 7c | NA | −73.6 | Similar to DINP |
| 7d | NA | | Similar to DINP |
| 8 | 161.7 | | NA |
| 9 | NA | | NA |
| 10 | NA | | Similar to DINP |
| 11 | NA | | NA |
| 12 | 225.5 | | NA |
| 13 | 204.1 | | NA |
| 14 | 190.8 | | NA |
| 15 | 105.5 | | Very dark and stiffer than DINP |
| 16 | 228.2 | | More flex than DINP |
| 17 | 165.2 | | Similar to DINP |
| 18 | 86.6 | | Stiffer than DINP |
| 19 | 117.8 | | Similar to DINP |
| 20 | 259.5 | | Stiffer than DINP nad exudates |
| 21 | NA | | NA |
| 22 | NA | | Very flex colorless |
| 23 | NA | | Similar to DINP |
| 24 | NA | | More flex than DINP |

Example 25

A PVC plastisol was prepared according the ASTM D1755 method, by mixing in a Hobart mixer 150 grams of the plasticizer of Example 1 the 4-phenyl-benzoic acid isodecyl alcohol ester, 200 grams of PVC resin, and 6 grams of PVC stabilizer Thermcheck™ SP 1363 and at varying speeds for 10 minutes. The 1 hour plastisol viscosity after mixing was 4410 cP measured at a shear rate of 180 1/s. By comparison a DINP formulation prepared my the same procedure had a 1 hr plastisol viscosity of 2440 cp.

Weight losses after heating of this plastisol for 4 minutes at 200C were 0.21% versus 0.22% for a comparative example based on DINP and 0.24% for a comparative example based on DOTP. Dynamic mechanical analysis of the plastisols as they were heated to final fusion, gave an initial gelation temperature of 91C, final gelation temperature of 116C, and a fusion temperature of 166 C. The comparative example based on DINP have a gelation temperature of 90C, a final gelation temperature of 128 C and a fusion temperature of 173 C.

Thin layers (10-15 mils) of the plastisol were fused in a Werner Mathys forced air oven for 3 minutes at 180 C, then combined and molded at 170 C for 15 minutes into test plaques.

PCT and EP CLAUSES

1. Compounds of the formula

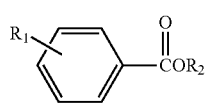

wherein $R_1$ is a saturated or unsaturated cyclic hydrocarbon optionally substituted with an alkyl and/or an OXO-ester, and $R_2$ is a hydrocarbon residue of a $C_4$ to $C_{14}$ OXO-alcohol.

2. The compounds of clause 1, wherein $R_1$ is located at the ortho-, meta- or para-position.

3. The compounds of clause 1, wherein $R_1$ is phenyl located at the para-position.

4. The compounds of clause 3, wherein $R_1$ is an alkyl and/or an OXO-ester-substituted phenyl at the ortho-, meta-, or para-position.

5. The compounds of clause 1, wherein $R_1$ is an alkyl and/or an OXO-ester-substituted cyclohexyl at the ortho-, meta-, or para-position.

6. The compounds of any of the preceding clauses, wherein $R_2$ is the hydrocarbon residue of a $C_5$ to $C_{10}$ OXO-alcohol averaging from 0.2 to 5.0 branches per residue.

7. The compounds of any of the preceding clauses, wherein the hydrocarbon residue averages from 0.05 to 0.4 branches per residue at the alcoholic beta carbon.

8. The compounds of any of the preceding clauses, wherein the hydrocarbon residue averages at least 1.3 to 5.0 methyl branches per residue.

9. The compounds of any of the preceding clauses, wherein the hydrocarbon residue averages from 0.35 to 1.5 pendant methyl branches per residue.

10. A process for making compounds of the formula:

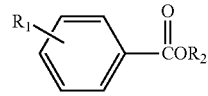

wherein $R_1$ is a cyclic hydrocarbon optionally substituted with an alkyl and/or an OXO-ester, and $R_2$ is a hydrocarbon residue of a $C_4$ to $C_{14}$ OXO-alcohol, comprising the steps of: reacting benzene or alkylated benzene under conditions appropriate to form alkylated biphenyl; optionally alkylating biphenyl to form said alkylated biphenyl; oxidizing the alkyl group(s) on said alkylated biphenyl to form at least one acid group; and reacting said acid group(s) with an OXO-alcohol under esterification conditions to form said compounds.

11. The process of clause 10, wherein said reacting step is conducted with benzene, and said optional alkylating step is conducted with an alcohol.

12. The process of clauses 10-11, wherein said alcohol is methanol and said alkylating step is conducted in the presence of an acid catalyst.

13. The process of clause 10, wherein said reacting step is conducted with benzene, further comprising the steps of hydroalkylating benzene by reacting benzene in the presence of $H_2$ to hydrogenate one mole of said benzene to form cyclohexene, alkylating benzene with said cyclohexene to form cyclohexylbenzene; dehydrogenating said cyclohexylbenzene to form biphenyl; and alkylating one or both aromatic moieties of said biphenyl to form said alkylated biphenyl.

14. The process of clause 13, wherein said hydroalkylating step is conducted in the presence of a hydrogenation catalyst, said alkylating step is conducted with an alkylation catalyst, and said dehydrogenating step is conducted with a dehydrogenation catalyst.

15. The process of clause 14, wherein said hydrogenation catalyst is selected from the group consisting of platinum, palladium, ruthenium, nickel, zinc, tin, cobalt, or a combination of these metals, with palladium being particularly advantageous; said alkylation catalyst is selected from the group consisting of Zeolite, mixed metal oxides and said dehydrogenation catalyst is selected from the group consisting of platinum, pladium, Ru, Rh, nickel, zinc, tin, cobalt and combinations thereof.

16. The process of clause 10, wherein said reacting step is conducted with benzene in the presence of oxygen and an oxidative coupling catalyst, forming biphenyl, further comprising the step of: alkylating one or both aromatic moieties of said biphenyl to form said alkylated biphenyl.

17. The process of clause 16, wherein said alkylating step is conducted with an alkylation catalyst.

18. The process of clause 10, wherein the reacting step is conducted with toluene, further comprising the steps of: reacting toluene in the presence of $H_2$ and a hydrogenation catalyst to form methyl cyclohexene; reacting said methyl cyclohexene with toluene in the presence of an alkylation catalyst to form dimethyl cyclohexylbenzene; and dehydrogenating said dimethyl cyclohexylbenzene in the presence of a dehydrogenation catalyst to form the alkylated biphenyl, which is dimethyl-biphenyl.

19. A polymer composition comprising a thermoplastic polymer and at least one plasticizer of the formula:

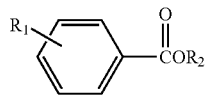

wherein $R_1$ is a saturated and unsaturated cyclic hydrocarbon optionally substituted with an alkyl and/or an OXO-ester, and $R_2$ is a hydrocarbon residue of a $C_4$ to $C_{14}$ OXO-alcohol.

20. The polymer composition of clause 19, wherein the thermoplastic polymer is selected from the group consisting of vinyl chloride resins, polyesters, polyurethanes, ethylene-vinyl acetate copolymer, rubbers, poly(meth)acrylics and combinations thereof.

The meanings of terms used herein shall take their ordinary meaning in the art; reference shall be taken, in particular, to Handbook of Petroleum Refining Processes, Third Edition, Robert A. Meyers, Editor, McGraw-Hill (2004). In addition, all patents and patent applications, test procedures (such as ASTM methods), and other documents cited herein are fully incorporated by reference to the extent such disclosure is not inconsistent with this disclosure and for all jurisdictions in which such incorporation is permitted. Also, when numerical lower limits and numerical upper limits are listed herein, ranges from any lower limit to any upper limit are contemplated. Note further that Trade Names used herein are indicated by a ™ symbol or ® symbol, indicating that the names may be protected by certain trademark rights, e.g., they may be registered trademarks in various jurisdictions.

The disclosure has been described above with reference to numerous embodiments and specific examples. Many variations will suggest themselves to those skilled in this art in light of the above detailed description. All such obvious variations are within the full intended scope of the appended claims.

What is claimed is:
1. Compounds of the formula

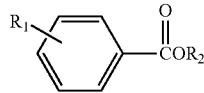

wherein $R_1$ is a saturated or unsaturated cyclic hydrocarbon substituted with an alkyl and/or an OXO-ester, and $R_2$ is a hydrocarbon residue of a $C_4$ to $C_{14}$ OXO-alcohol.

2. The compounds of claim 1, wherein $R_1$ is located at the ortho-, meta- or para-position.

3. The compounds of claim 1, wherein $R_1$ is phenyl located at the para-position.

4. The compounds of claim 3, wherein $R_1$ is an alkyl and/or an OXO-ester-substituted phenyl at the ortho-, meta-, or para-position.

5. The compounds of claim 1, wherein $R_1$ is an alkyl and/or an OXO-ester-substituted cyclohexyl at the ortho-, meta-, or para-position.

6. The compounds of claim 1, wherein $R_2$ is the hydrocarbon residue of a $C_5$ to $C_{10}$ OXO-alcohol averaging from 0.2 to 5.0 branches per residue.

7. The compounds of claim 1, wherein the hydrocarbon residue averages from 0.05 to 0.4 branches per residue at the alcoholic beta carbon.

8. Compounds of the formula:

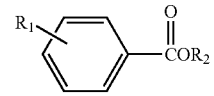

wherein $R_1$ is a saturated or unsaturated cyclic hydrocarbon optionally substituted with an alkyl and/or an OXO-ester, and $R_2$ is a hydrocarbon residue of a $C_4$ t $C_{14}$ OXO-alcohol, wherein the hydrocarbon residue averages at least 1.3 to 5.0 methyl branches per residue.

9. The compounds of claim 1, wherein the hydrocarbon residue averages from 0.35 to 1.5 pendant methyl branches per residue.

10. The compounds of claim 1, which are represented by the formula:

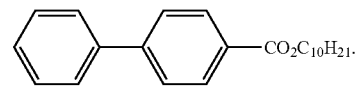

11. The compounds of claim 1, which are represented by the formula:

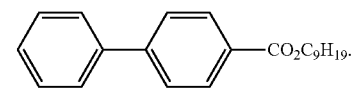

12. The compounds of claim 1, which are represented by the formula:

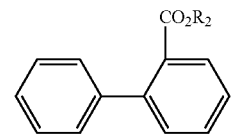

wherein $R_2$ is $C_9H_{19}$, $C_{10}H_{21}$ or $C_{13}H_{27}$.

13. The compounds of claim 1, which are represented by the formula:

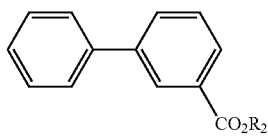

wherein $R_2$ is $C_9H_{19}$, $C_{10}H_{21}$, or $C_{13}H_{27}$.

14. The compounds of claim 1, which are represented by a mixture of the following at any ratio:

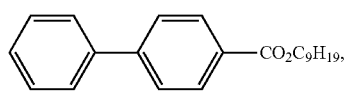

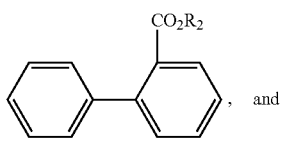, and

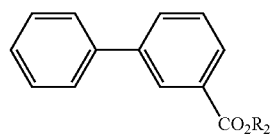

wherein $R_2$ is $C_9H_{19}$, $C_{10}H_{21}$, or $C_{13}H_{27}$.

15. A compound represented by the formula:

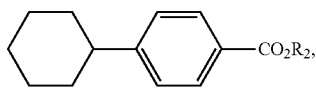

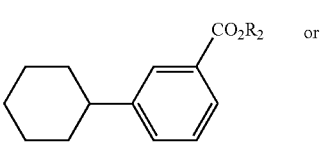 or

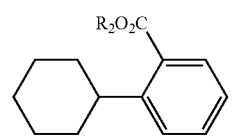

wherein $R_2=C_9H_{19}$, $C_{10}H_{21}$, or $C_{13}H_{27}$.

16. A mixture of the compounds of claim 15 at any ratio.

17. A compound represented by the formula:

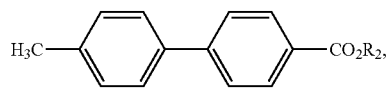

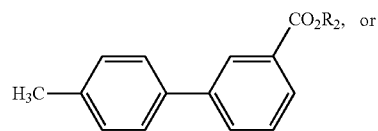, or

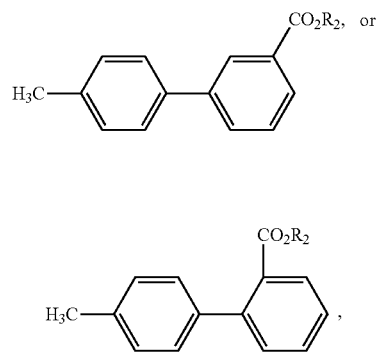, wherein $R_2=C_9H_{19}$, $C_{10}H_{21}$, or $C_{13}H_{27}$.

18. A compound represented by the formula:

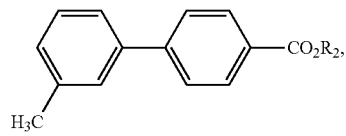

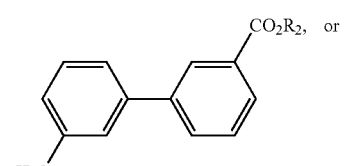 or

wherein $R_2=C_9H_{19}$ or $C_{10}H_{21}$, or $C_{13}H_{27}$.

19. A compound represented by the formula:

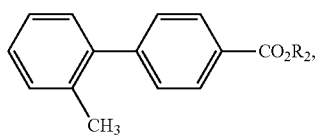

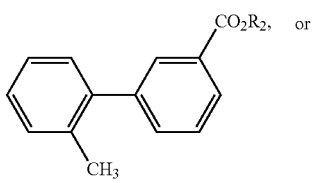 or
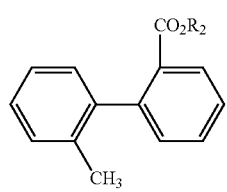
wherein $R_2 = C_9H_{19}$, $C_{10}H_{21}$, or $C_{13}H_{27}$.
20. A mixture of the compounds represented by the formulae below at any ratio:
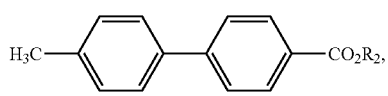
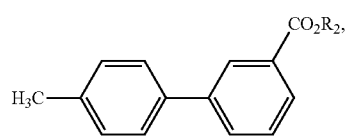
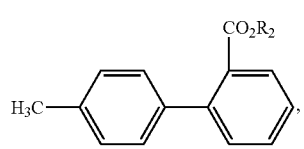
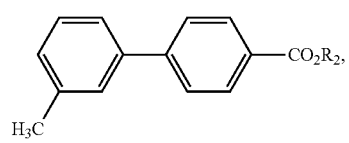
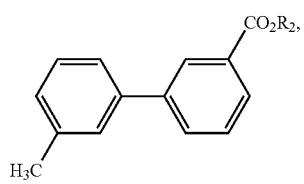
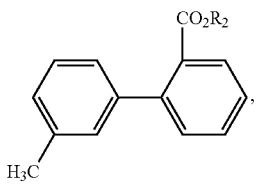
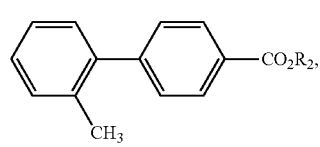
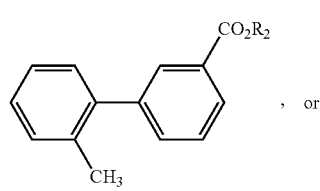
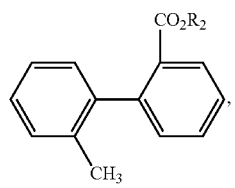 , or
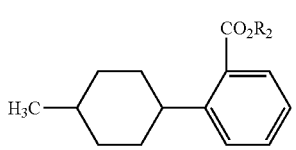
wherein $R_2 = C_9H_{19}$, $C_{10}H_{21}$, or $C_{13}H_{27}$.
21. A compound represented by the formula:
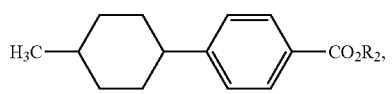
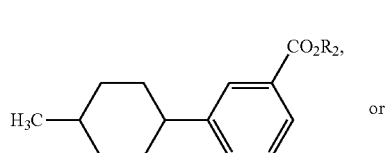 or
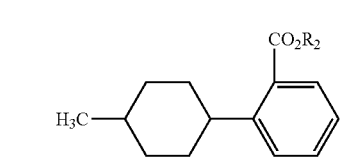
wherein $R_2 = C_9H_{19}$, $C_{10}H_{21}$, or $C_{13}H_{27}$.

22. A compound represented by the formula:
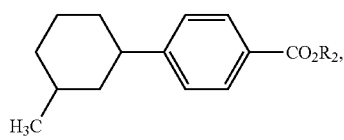
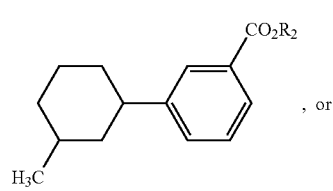, or
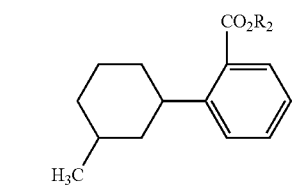
wherein $R_2 = C_9H_{19}$, $C_{10}H_{21}$, or $C_{13}H_{27}$.
23. A compound represented by the formula:
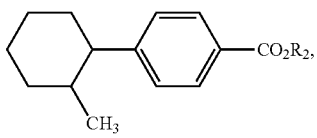
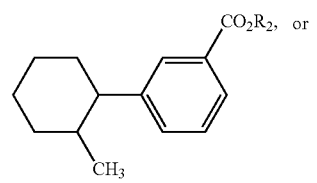, or
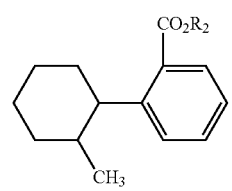
wherein $R_2 = C_9H_{19}$, $C_{10}H_{21}$, or $C_{13}H_{27}$.
24. A mixture of the compounds represented below at any ratio:
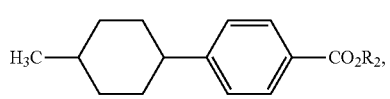
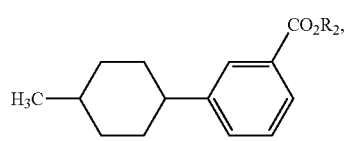
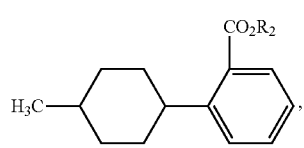
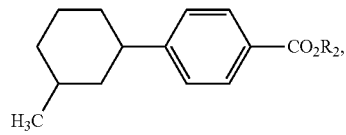
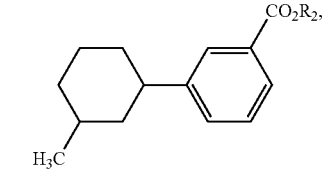
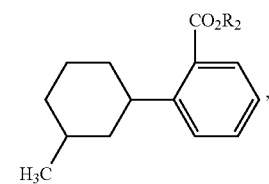
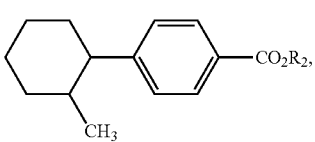

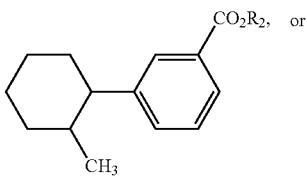

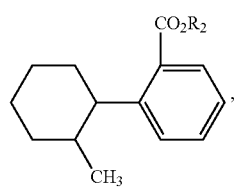

wherein $R_2=C_9H_{19}$, $C_{10}H_{21}$, or $C_{13}H_{27}$.

25. A composition comprising a mixture of the compounds of claims 20 and 24 at any ratio.

26. A process for making compounds of the formula:

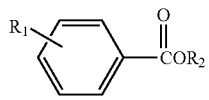

wherein $R_1$ is a cyclic hydrocarbon substituted with an alkyl and/or an OXO-ester, and $R_2$ is a hydrocarbon residue of a $C_4$ to $C_{14}$ OXO-alcohol, comprising the steps of:
reacting benzene or alkylated benzene under conditions appropriate to form alkylated biphenyl;
optionally alkylating biphenyl to form said alkylated biphenyl;
oxidizing the alkyl group(s) on said alkylated biphenyl to form at least one acid group; and
reacting said acid group(s) with an OXO-alcohol under esterification conditions to form said compounds.

27. The process of claim 26, wherein said reacting step is conducted with benzene, and said optional alkylating step is conducted with an alcohol.

28. The process of claim 27, wherein said alcohol is methanol and said alkylating step is conducted in the presence of an acid catalyst.

29. The process of claim 26, wherein said reacting step is conducted with benzene, further comprising the steps of:
hydroalkylating benzene by reacting benzene in the presence of $H_2$ to hydrogenate one mole of said benzene to form cyclohexene,
alkylating benzene with said cyclohexene to form cyclohexylbenzene; dehydrogenating said cyclohexylbenzene to form biphenyl; and
alkylating one or both aromatic moieties of said biphenyl to form said alkylated biphenyl.

30. The process of claim 29, wherein said hydroalkylating step is conducted in the presence of a hydrogenation catalyst, said alkylating step is conducted with an alkylation catalyst, and said dehydrogenating step is conducted with a dehydrogenation catalyst.

31. The process of claim 30, wherein said hydrogenation catalyst is selected from the group consisting of platinum, palladium, ruthenium, nickel, zinc, tin, cobalt, or a combination of these metals, said alkylation catalyst is selected from the group consisting of Zeolite, mixed metal oxides and said dehydrogenation catalyst is selected from the group consisting of platinum, pladium, Ru, Rh, nickel, zinc, tin, cobalt and combinations thereof.

32. The process of claim 26, wherein said reacting step is conducted with benzene in the presence of oxygen and an oxidative coupling catalyst, forming biphenyl, further comprising the step of: alkylating one or both aromatic moieties of said biphenyl to form said alkylated biphenyl.

33. The process of claim 32, wherein said alkylating step is conducted with an alkylation catalyst.

34. The process of claim 26, wherein the reacting step is conducted with toluene, further comprising the steps of:
reacting toluene in the presence of $H_2$ and a hydrogenation catalyst to form methyl cyclohexene,
reacting said methyl cyclohexene with toluene in the presence of an alkylation catalyst to form dimethyl cyclohexylbenzene; and
dehydrogenating said dimethyl cyclohexylbenzene in the presence of a dehydrogenation catalyst to form the alkylated biphenyl, which is dimethyl-biphenyl.

35. A polymer composition comprising a thermoplastic polymer and at least one plasticizer of the formula:

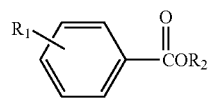

wherein $R_1$ is a saturated and unsaturated cyclic hydrocarbon substituted with an alkyl and/or an OXO-ester, and $R_2$ is a hydrocarbon residue of a $C_4$ to $C_{14}$ OXO-alcohol.

36. The polymer composition of claim 35, wherein the thermoplastic polymer is selected from the group consisting of vinyl chloride resins, polyesters, polyurethanes, ethylene-vinyl acetate copolymer, rubbers, poly(meth)acrylics and combinations thereof.

37. The polymer composition of claim 35, wherein the thermoplastic polymer is polyvinylchloride.

38. Compounds of the formula

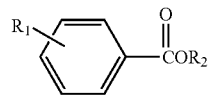

wherein $R_1$ is a saturated cyclic hydrocarbon optionally substituted with an alkyl and/or an OXO-ester, and $R_2$ is a hydrocarbon residue of a $C_4$ to $C_{14}$ OXO-alcohol.

39. The compound of claim 1, where $R_2$ contains mixed alkyl isomer residues of $C_4$ to $C_{13}$ OXO-alcohols.

40. The compound of claim 1, where $R_1$ contains mixed alkyl isomer residues of $C_4$ to $C_{13}$ OXO-alcohols.

* * * * *